United States Patent
Miyake

(10) Patent No.: US 8,138,367 B2
(45) Date of Patent: Mar. 20, 2012

(54) PROCESS FOR PRODUCTION OF AROMATIC CARBONATE

(75) Inventor: Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 640 days.

(21) Appl. No.: 11/793,997

(22) PCT Filed: Dec. 9, 2005

(86) PCT No.: PCT/JP2005/022683
§ 371 (c)(1),
(2), (4) Date: Jun. 25, 2007

(87) PCT Pub. No.: WO2006/067982
PCT Pub. Date: Jun. 29, 2006

(65) Prior Publication Data
US 2008/0097116 A1    Apr. 24, 2008

(30) Foreign Application Priority Data
Dec. 24, 2004 (JP) .................. 2004-373401

(51) Int. Cl.
*C07C 68/00* (2006.01)
(52) U.S. Cl. .................... 558/260; 558/274
(58) Field of Classification Search .................. None
See application file for complete search history.

(56) References Cited

U.S. PATENT DOCUMENTS

| | | | |
|---|---|---|---|
| 4,045,464 A | 8/1977 | Romano et al. | |
| 4,182,726 A | 1/1980 | Illuminati et al. | |
| 4,252,737 A | 2/1981 | Krimm et al. | |
| 4,410,464 A | 10/1983 | Hallgren | |
| 4,552,704 A | 11/1985 | Mark | |
| 4,554,110 A | 11/1985 | Mark | |
| 4,609,501 A | 9/1986 | Mark | |
| 5,210,268 A | 5/1993 | Fukuoka et al. | |
| 5,705,673 A * | 1/1998 | Rivetti et al. | 558/270 |
| 2005/0080274 A1 | 4/2005 | Miyake et al. | |
| 2005/0240045 A1 | 10/2005 | Miyake et al. | |

FOREIGN PATENT DOCUMENTS

| | | |
|---|---|---|
| EP | 0 560 159 A1 | 9/1993 |
| JP | 51-75044 | 6/1976 |
| JP | 51-105032 | 9/1976 |
| JP | 54-48732 | 4/1979 |
| JP | 54-48733 | 4/1979 |
| JP | 54-63023 | 5/1979 |
| JP | 56-25138 | 3/1981 |
| JP | 56-123948 | 9/1981 |
| JP | 56-123949 | 9/1981 |
| JP | 57-176932 | 10/1982 |
| JP | 57-183745 | 11/1982 |
| JP | 58-185536 | 10/1983 |
| JP | 60-169444 | 9/1985 |
| JP | 60-169445 | 9/1985 |
| JP | 60-173016 | 9/1985 |
| JP | 61-172852 | 8/1986 |
| JP | 61-291545 | 12/1986 |
| JP | 62-277345 | 12/1987 |
| JP | 1-93560 | 4/1989 |
| JP | 1-265062 | 10/1989 |
| JP | 1-265063 | 10/1989 |
| JP | 1-265064 | 10/1989 |
| JP | 4-9358 | 1/1992 |
| JP | 4-224547 | 8/1992 |
| JP | 6-157410 | 6/1994 |
| JP | 9-169704 | 6/1997 |
| JP | 10-152455 | 6/1998 |
| JP | 2000-63332 | 2/2000 |
| JP | 2000-727221 | 3/2000 |
| JP | 2000-307400 | 11/2000 |
| JP | 2003-238487 | 8/2003 |
| JP | 2004-75577 | 3/2004 |
| JP | 2004-307400 | 11/2004 |
| JP | 2004-323384 | 11/2004 |
| WO | 91/09832 | 7/1991 |
| WO | 92/18458 | 10/1992 |
| WO | 03/055840 | 7/2003 |
| WO | 2004/014840 | 2/2004 |

OTHER PUBLICATIONS

Aliphatic, http://www.thefreedictionary.com/aliphatic (2003).*

(Continued)

*Primary Examiner* — Sun Jae Y Loewe
(74) *Attorney, Agent, or Firm* — Staas & Halsey LLP

(57) ABSTRACT

The present invention provides a process for the production of an aromatic carbonate, comprising the steps of: continuously feeding an aliphatic carbonate represented by following general formula (1) as a starting material, an aromatic monohydroxy compound represented by following general formula (2) as a reactant, and a metal-containing catalyst into a stage above the bottom of a first multi-stage distillation column so as to bring about reaction; continuously withdrawing from the reaction system in a gaseous form a low boiling point component containing an alcohol by-produced in the reaction; and continuously withdrawing from a lower portion of the column in a liquid form an aromatic carbonate represented by following general formula (3) obtained from the starting material and the reactant

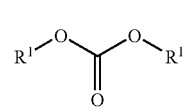
(1)

$Ar^1OH$ (2)

wherein $R^1$ in general formulae (1) and (2) represents an aliphatic group having 4 to 6 carbon atoms, and $Ar^1$ represents an aromatic group having 5 to 30 carbon atoms

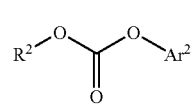
(3)

wherein $R^2$ and $Ar^2$ in general formulae (3) are the same as $R^1$ and $Ar^1$ in the starting material and the reactant, respectively.

17 Claims, 3 Drawing Sheets

OTHER PUBLICATIONS

Aliphatic-2, http://dictionary.babylon.com/Aliphatic%20compound (2009).*
U.S. Appl. No. 11/793,786, filed Dec. 2005, Miyake*
Saito et al., caplus an 1968:22474.*
International Search Report Of International Published Application No. PCT/JP2005/022683 (mailed Feb. 14, 2006).

* cited by examiner

PROCESS FOR PRODUCTION OF AROMATIC CARBONATE

CROSS REFERENCE TO RELATED APPLICATIONS

This application is based on and claims priority benefit to International application PCT/JP2005/022683, filed on Dec. 9, 2005 and Japanese Application No. 2004-373401 filed on Dec. 24, 2004, the disclosures of which are hereby incorporated herein by reference.

TECHNICAL FIELD

The present invention relates to a process for the continuous production of aromatic carbonates. More particularly, the present invention relates to a process for continuously producing aromatic carbonates containing an aliphatic-aromatic carbonate, a diaryl carbonate, or a mixture thereof with a high yield by reacting an aliphatic carbonate and an aromatic hydroxy compound together.

BACKGROUND ART

Aromatic carbonates are useful, for example, as raw materials for the production of aromatic polycarbonates, which in recent years have become increasingly used as engineering plastics, without using toxic phosgene. As processes for the production of aromatic carbonates, a process of subjecting an alkyl carbonate and an aromatic monohydroxy compound to transesterification, a process of subjecting an alkyl aryl carbonate and an aromatic monohydroxy compound to transesterification, and a process of subjecting two molecules of the same alkyl aryl carbonate to transesterification, i.e. disproportionation, are known. Typical reactions included under processes for the production of an aromatic carbonate or a mixture of aromatic carbonates through reaction between an alkyl carbonate and an aromatic monohydroxy compound are represented by following reaction formulae (E1), (E2), (E3) and (E4):

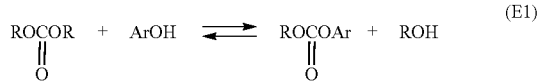
(E1)

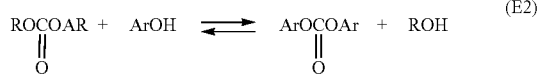
(E2)

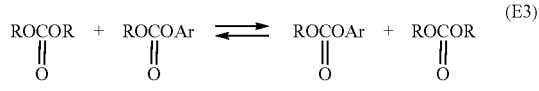
(E3)

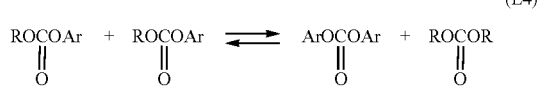
(E4)

(wherein R represents an alkyl group, and Ar represents an aromatic group. Reaction formulae (E3) and (E4) are transesterification reactions between the same molecular species, with reaction formula (E4) also generally being referred to as a disproportionation reaction).

The above reactions of (E1) to (E4) are all equilibrium reactions. For the reactions of (E1) and (E4) in particular, the equilibrium is biased markedly toward the original system, and the reaction rate is slow, and hence the aromatic carbonate yield is low, and thus there have been many difficulties in industrial production. Several proposals have been made to improve on the above difficulties, but most of these have related to development of a catalyst to increase the reaction rate. For example, Lewis acids such as transition metal halides and Lewis acid-forming compounds (see, for example, Patent Document 1: Japanese Patent Application Laid-Open No. 51-105032, Patent Document 2: Japanese Patent Application Laid-Open No. 56-123948, Patent Document 3: Japanese Patent Application Laid-Open No. 56-123949), tin compounds such as organo-tin alkoxides and organo-tin oxides (see, for example, Patent Document 4: Japanese Patent Application Laid-Open No. 54-48733, Patent Document 5: Japanese Patent Application Laid-Open No. 54-63023, Patent Document 6: Japanese Patent Application Laid-Open No. 60-169444, Patent Document 7: Japanese Patent Application Laid-Open No. 60-169445, Patent Document 8: Japanese Patent Application Laid-Open No. 62-277645, Patent Document 9: Japanese Patent Application Laid-Open No. 1-265063), salts and alkoxides of alkali metals and alkaline earth metals (see, for example, Patent Document 10: Japanese Patent Application Laid-Open No. 56-25138), lead compounds (see, for example, Patent Document 11: Japanese Patent Application Laid-Open No. 57-176932), complexes of metals-such as copper, iron and zirconium (see, for example, Patent Document 12: Japanese Patent Application Laid-Open No. 57-183745), titanic acid esters (see, for example, Patent Document 13: Japanese Patent Application Laid-Open No. 58-185536), mixtures of a Lewis acid and a protonic acid (see, for example, Patent Document 14: Japanese Patent Application Laid-Open No. 60-173016), compounds of Sc, Mo, Mn, Bi, Te or the like (see, for example, Patent Document 15: Japanese Patent Application Laid-Open No. 1-265064), ferric acetate (see, for example, Patent Document 16: Japanese Patent Application Laid-Open No. 61-172852), and so on have been proposed. However, the main reason that the aromatic carbonate yield is low is not the reaction rate being slow but rather the equilibrium being biased markedly toward the original system, and hence improving the reaction rate through catalyst development cannot be said to be effective in improving the aromatic carbonate yield.

Regarding the reaction represented by above formula (E1), processes are known in which the by-produced alcohol is removed from the reaction system so as to shift the equilibrium toward the product system and thus promote the reaction. For example, batch reaction systems using a reactor provided with a distillation column are known (see, for example, Patent Document 2: Japanese Patent Application Laid-Open No. 56-123948, Patent Document 6: Japanese Patent Application Laid-Open No. 60-169444, Patent Document 7: Japanese Patent Application Laid-Open No. 60-169445, and Patent Document 14: Japanese Patent Application Laid-Open No. 60-173016). However, to make the aromatic carbonate yield high, operation must be carried out for a very long period of time, and moreover a large apparatus is required relative to the amount produced of the desired product; for such reasons, such a batch reaction system is not industrially practicable. As other processes in which the by-produced alcohol is removed from the reaction system, there have been proposed, for example, for the reaction between dimethyl carbonate and phenol, a process in which by-produced methanol is distilled off by azeotropy together with an azeotrope-forming agent (see, for example, Patent Document 17: Japanese Patent Application Laid-Open No. 54-48732 (corresponding to Patent Document 18: West German Patent Application Laid-Open No. 736063, and Patent Document 19: U.S. Pat. No. 4,252,737), Patent Document 20: Japanese Patent Application Laid-Open No. 61-291545), and a process in which the by-produced methanol is removed by being adsorbed onto a molecular sieve (see, for example, Patent Document 21: Japanese Patent Application Laid-Open No. 58-185536 (corresponding to Patent Document 22: U.S. Pat. No. 410,464)).

A process is also known in which aromatic carbonates are produced using a multi-stage distillation column so as to promote removal of the by-produced alcohol from the reaction system. In this process, a dialkyl carbonate and an aromatic hydroxy compound are continuously fed into a multi-stage distillation column, and reaction is carried out continuously in the distillation column, while continuously withdrawing by distillation a low boiling point component containing a by-produced alcohol from an upper portion of the column, and continuously withdrawing a component containing produced aromatic carbonates from a lower portion of the column (see, for example, Patent Document 23: Japanese Patent Application Laid-Open No. 4-224547).

Regarding the disproportionation reaction represented by above formula (E4), processes are known in which the by-produced dialkyl carbonate is removed from the reaction system so as to shift the equilibrium toward the product system and thus promote the reaction. Examples include a process in which an alkyl aryl carbonate is continuously fed into a multi-stage distillation column, and reaction is carried out continuously in the distillation column, while continuously withdrawing by distillation a low boiling point component containing the by-produced dialkyl carbonate from an upper portion of the column, and continuously withdrawing a component containing a produced diaryl carbonate from a lower portion of the column (see, for example, Patent Document 24: Japanese Patent Application Laid-Open No. 4-9358).

The reactions represented by above formulae (E1) to (E4) are generally promoted using a catalyst. The catalyst may be solid or liquid, and there have been reports regarding methods of feeding in the catalyst. For example, known methods include a method in which a titanium tetraalkoxide having alkoxy groups corresponding to the alkyl groups in a dialkyl carbonate used as a raw material is fed in, whereby contamination with by-produced material due to an alkyl alcohol by-produced from the catalyst is prevented (see, for example, Patent Document 25: Japanese Patent Application Laid-Open No. 2000-72721), a method in which, although it is known that the catalyst may precipitate out upon prolonged operation, a dialkyl carbonate, an aromatic hydroxy compound and a catalyst are continuously fed into a reactor, a by-produced alcohol is continuously withdrawn from a distillation column attached to the reactor, and aromatic carbonate containing an alkyl aryl carbonate, a diary carbonate, or a mixture thereof is withdrawn from the reactor, whereby clogging of the distillation column is prevented (see, for example, Patent Document 26: Japanese Patent Application Laid-Open No. 6-157410), and a method in which clogging is prevented by separating the feeding position for a catalyst from the feeding position for a dialkyl carbonate and an aromatic hydroxy compound (see, for example, Patent Document 27: Japanese Patent Application Laid-Open No. 2000-307400).

The catalyst used in such a reaction system is generally present dissolved in the reaction liquid under the reaction conditions, and moreover has a higher boiling point than that of the aromatic carbonates, and hence to obtain a high-purity aromatic carbonate from the liquid produced through the reaction, first a low boiling point component is removed from the reaction liquid, and then the diaryl carbonate in the high boiling point component is separated from the catalyst, thus purifying the diaryl carbonate. It is known that in this case the catalyst may be recovered as a high boiling point component, and may be recycled, or may have a deactivated component removed therefrom. An example of the process for separating out the catalyst is the process described in Patent Document 28 (Japanese Patent Application Laid-Open No. 9-169704). Moreover, a process in which separating out of the catalyst is carried out by using a catalyst having a low boiling point such as an alkylamine is also known (see, for example, Patent Document 29: Japanese Patent Application Laid-Open No. 2003-238487).

Although research has been carried out into processes for producing aromatic carbonates through reaction between a dialkyl carbonate and an aromatic hydroxy compound as described above, in most cases (not only the above examples), the dialkyl carbonate or the hydroxy compound is used in excess. A process in which one of these compounds is used in excess, and unreacted compound is recovered and reused has very poor energy efficiency. Furthermore, in addition to the equilibrium being unfavorable, in most of the publicly known production processes described above, dimethyl carbonate is used as the dialkyl carbonate. Dimethyl carbonate has a low boiling point of approximately 90° C., and moreover forms an azeotrope with methanol by-produced in the reaction. The azeotrope has a lower boiling point than dimethyl carbonate, and hence when removing the by-produced methanol from the system, dimethyl carbonate is also removed at the same time. To increase the reaction ratio, it is thus necessary to feed in the dimethyl carbonate in an amount several times that consumed in the reaction, and hence the energy efficiency has been very poor.

Processes in which excessively used energy is recovered and reused are also known. For example, a process is known in which vapor produced in a reactor is brought back into contact with the reaction liquid indirectly so as to heat the reaction liquid and thus improve the energy efficiency (see, for example, Patent Document 30: Japanese Patent Application Laid-Open No. 2004-75577). However, because dimethyl carbonate is used as the dialkyl carbonate, there is the problem described above that to remove methanol by-produced in the reaction from the system, dimethyl carbonate must be removed from the system at the same time.

A process in which a dialkyl carbonate that does not form an azeotrope with the alcohol by-produced in the reaction is used is also known (see, for example, Patent Document 31: Japanese Patent Application Laid-Open No. 10-152455). In this process, there is a suitable difference in boiling point between the alcohol by-produced in the reaction and the dialkyl carbonate, and hence it is easy to separate off only the alcohol. However, because a batch reaction system is used, a large apparatus is required relative to the amount produced of the desired product, and hence the process is not industrially practicable. Moreover, a process in which a multi-stage distillation column is used, and a dialkyl carbonate that does not form an azeotrope with the alcohol by-produced in the reaction is used is also known (see, for example, Patent Document 27: Japanese Patent Application Laid-Open No. 2000-307400). In this process, under a condition of excess aromatic hydroxy compound, the catalyst is fed into only the bottom of the column, and hence the reaction proceeds only in the bottom of the column, and thus a problem of deposition of a catalyst-derived component on structures in the distillation column is resolved; however, because the reaction proceeds only in the bottom of the column, the multi-stage distillation column thereabove is provided only for carrying out separation by distillation on the compounds having a vapor pressure (the dialkyl carbonate, phenol, the alcohol by-produced in the reaction, etc.), and a large excess of the aromatic hydroxy compound such that the starting material (i.e. aliphatic carbonate)/reactant (i.e. aromatic hydroxy compound) molar ratio is 0.01 must be used to shift the equilibrium toward the product system in only the bottom of the column, and thus the aromatic carbonate yield obtained is low based on both the starting material (the aliphatic carbonate) and the reactant (the aromatic hydroxy compound).

In the above publicly known processes, there are problems that either the dialkyl carbonate or the aromatic hydroxy compound is used in excess, and excess energy is used, and furthermore there is a problem that the aromatic carbonate(s) comprising an alkyl aryl carbonate, a diaryl carbonate, or a mixture thereof cannot be obtained with a high yield.

DISCLOSURE OF INVENTION

It is an object of the present invention to provide a process for production of aromatic carbonates with high yield in which in the case of carrying out aromatic carbonate production by reacting an aliphatic carbonate and an aromatic monohydroxy compound together and removing a by-produced alcohol from the reaction system, there are no drawbacks as described above, without using an excess of the aliphatic carbonate or aromatic monohydroxy compound, and without using excess energy.

The present inventors have carried out assiduous studies to attain the above object, and as a result have arrived at the present invention after discovering that, in the case of carrying out aromatic carbonate production by reacting an aliphatic carbonate and an aromatic monohydroxy compound together and removing a by-produced alcohol from the reaction system, the above object can be attained by reacting a specified aliphatic carbonate and a specified aromatic monohydroxy compound together. According to the present invention, an aromatic carbonate can be produced with a higher yield than in a publicly known aromatic carbonate production process, without using an excess of a raw material, and without using excess energy.

That is, the present invention provides:

[1] a process for the production of an aromatic carbonate, comprising the step of: continuously feeding an aliphatic carbonate represented by following general formula (1) as a starting material, an aromatic monohydroxy compound represented by following general formula (2) as a reactant, and a metal-containing catalyst into a stage above a bottom of a first multi-stage distillation column so as to bring about reaction; and continuously withdrawing from a reaction system in a gaseous form a low boiling point component containing an alcohol by-produced in the reaction, and continuously withdrawing from a lower portion of the column in a liquid form an aromatic carbonate represented by following general formula (3) obtained from the starting material and the reactant,

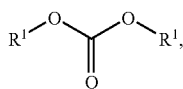

(1)

(2), wherein $R^1$ in general formulae (1) and (2) represents an aliphatic group having 4 to 6 carbon atoms, and $Ar^1$ represents an aromatic group having 5 to 30 carbon atoms,

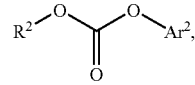

(3)

wherein $R^2$ and $Ar^2$ in general formulae (3) are the same as $R^1$ and $Ar^1$ in the starting material and the reactant, respectively,

[2] the process according to item [1], wherein said aromatic carbonate may comprise a diaryl carbonate represented by following general formula (4):

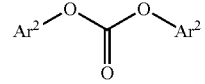

(4)

wherein $R^2$ and $Ar^2$ in general formulae (4) are the same as $R^1$ and $Ar^1$ in the starting material and the reactant, respectively,

[3] the process according to item [1], wherein $R^1$ in the aliphatic carbonate represented by general formula (1) is a saturated aliphatic group having 4 to 6 carbon atoms,

[4] the process according to any one of items [1] to [3], wherein $R^1$ in the aliphatic carbonate represented by general formula (1) is a saturated aliphatic group having 5 or 6 carbon atoms,

[5] the process according to any one of items [1] to [4], wherein $R^1$ in the aliphatic carbonate represented by general formula (1) is an alkyl group,

[6] the process according to any one of items [1] to [5], wherein the aromatic monohydroxy compound represented by general formula (2) comprises phenol,

[7] the process according to any one of items [1] to [6], wherein the column bottom temperature in said distillation column is in a range of from 150 to 250° C.,

[8] the process according to any one of items [1] to [7], wherein a molar ratio of the reactant to the starting material fed into said multi-stage distillation column is in a range of from 0.1 to 5,

[9] the process according to any one of items [1] to [8], wherein said metal-containing catalyst is dissolved in a liquid phase in said reaction, or is present in a liquid form during said reaction,

[10] the process according to item [9], wherein said metal-containing catalyst that is dissolved in a liquid phase in said reaction, or is present in a liquid form during said reaction comprises an organic titanate,

[11] the process according to item [10], wherein the organic titanate comprises an organic titanate having at least one Ti—O—Ti linkage therein,

[12] the process according to any one of items [1] to [11], wherein the first multi-stage distillation column has not less than two theoretical distillation stages therein, and the catalyst is made to be present in at least two of the stages,

[13] the process according to item [1], further comprising the steps of: continuously feeding into a second multi-stage distillation column the reaction liquid withdrawn from the lower portion of the first multi-stage distillation column in the process according to claim 1 either as is or after removing the starting material and/or reactant therefrom, so as to carry out a disproportionation reaction; continuously withdrawing in a gaseous form by distillation a low boiling point component containing an aliphatic carbonate by-produced in the reaction; and continuously withdrawing from a lower portion of the second multi-stage distillation column in a liquid form a diaryl carbonate represented by general formula (4),

[14] the process according to item [1] or [13], wherein the steps according to claim 13 are added to recycle the aliphatic carbonate for use as the starting material in item [1].

ADVANTAGEOUS EFFECT OF INVENTION

According to the present invention, a specified aliphatic carbonate and a specified aromatic monohydroxy compound are reacted together using a reactive distillation method in the presence of a catalyst, whereby an aromatic carbonate can be produced continuously with a high yield.

Figure 1:
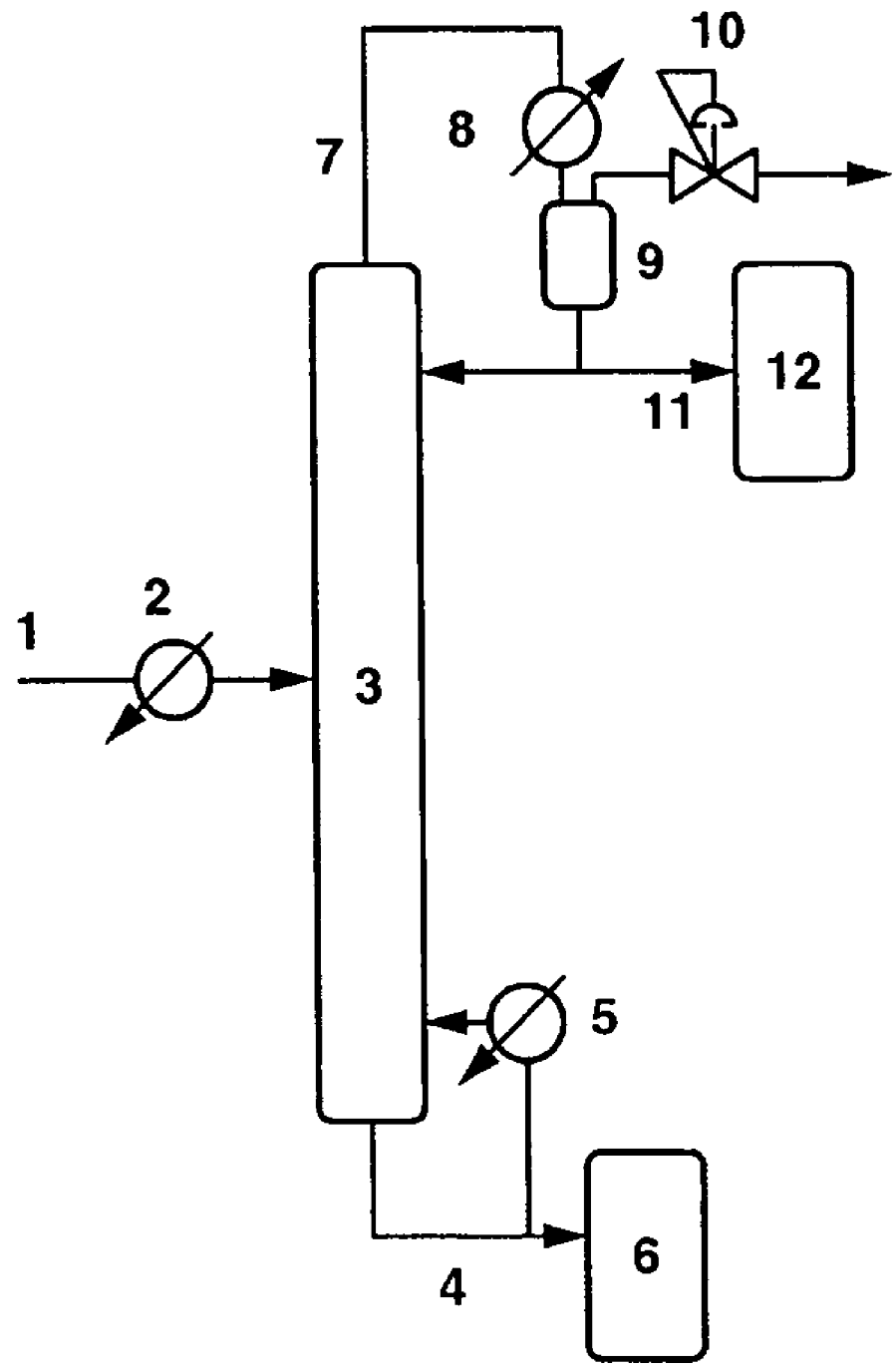
FIG. 1 is a process flow diagram for aromatic carbonate production according to the present invention.

1, 13: transfer line
4, 7, 11, 16, 19, 23, 25, 28, 31, 35, 37, 40, 43, 47, 49: conduit
2, 14, 26, 38: preheater
3, 15, 27, 39: multi-stage distillation column
8, 15, 32, 44: condenser
9, 21, 33, 45: gas-liquid separator (flash drum)
5, 17, 29, 41: reboiler
6, 12, 18, 24, 30, 36, 42, 48, 50: storage tank
10, 22, 34, 46: pressure-controlling valve

BEST MODE FOR CARRYING OUT THE INVENTION

Following is a detailed description of the present invention.
An aliphatic carbonate used in the present invention is one represented by following general formula (1):

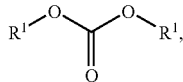
(1)

wherein $R^1$ in general formulae (1) represents an aliphatic group having 4 to 6 carbon atoms.

Examples of $R^1$ include a butyl group (isomers), a pentyl group (isomers), and a hexyl group (isomers).

Examples of aliphatic carbonates represented by above general formula (1) include dibutyl carbonate (isomers), dipentyl carbonate (isomers), and dihexyl carbonate (isomers). Of these aliphatic carbonates, ones preferably used in the present invention are aliphatic carbonates in which $R^1$ is a saturated aliphatic group, specifically a straight chain or branched alkyl group or other aliphatic group, having 4 to 6 carbon atoms. More preferable are aliphatic carbonates in which $R^1$ is an alkyl group or other saturated aliphatic group having 5 or 6 carbon atoms. Such a dialkyl carbonate may be produced using any process; one produced using a process previously proposed by the present inventors (WO 03055840, WO 04014840) can be preferably used.

An aromatic monohydroxy compound used in the present invention is one represented by following general formula (2):

 (2), wherein, $Ar^1$ represents an aromatic group having 5 to 30 carbon atoms.

Examples of such aromatic groups include a phenyl group and various alkylphenyl groups, for example phenyl, tolyl (isomers), xylyl (isomers), trimethylphenyl (isomers), tetramethylphenyl (isomers), ethylphenyl (isomers), propylphenyl (isomers), butylphenyl (isomers), diethylphenyl (isomers), methylethylphenyl (isomers), pentylphenyl (isomers), hexylphenyl (isomers) and cyclohexylphenyl (isomers); various alkoxyphenyl groups such as methoxyphenyl (isomers), ethoxyphenyl (isomers) and butoxyphenyl (isomers); various halogenated phenyl groups such as fluorophenyl (isomers), chlorophenyl (isomers), bromophenyl (isomers), chloro(methyl)phenyl (isomers) and dichlorophenyl (isomers); and various substituted phenyl groups represented by following general formula (5):

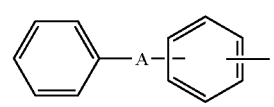
(5)

wherein A represents a single bond, a bivalent group such as —O—, —S—, —CO— or —SO$_2$—, an alkylene group or substituted alkylene group represented by following formula (6), or a cycloalkylene group represented by following formula (7), and the aromatic rings may be substituted with substituents such as lower alkyl groups, lower alkoxy groups, ester groups, hydroxy groups, nitro groups, halogen atoms, or cyano groups:

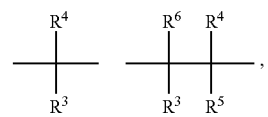
(6)

wherein $R^3$, $R^4$, $R^5$ and $R^6$ are each independently a hydrogen atom, a lower alkyl group, a cycloalkyl group, an aryl group or an aralkyl group, which in some cases may be substituted with halogen atoms or an alkoxy group:

(7)

wherein k is an integer from 3 to 11, and the hydrogen atoms may be substituted with lower alkyl groups, aryl groups, halogen atoms or the like.

Further examples of the above aromatic groups include a naphthyl group and various substituted naphthyl groups, for example naphthyl (isomers), methylnaphthyl (isomers), dimethylnaphthyl (isomers), chloronaphthyl (isomers), methoxynaphthyl (isomers) and cyanonaphthyl (isomers); and various optionally substituted heteroaromatic groups such as pyridyl (isomers), coumaryl (isomers), quinolyl (isomers), methylpyridyl (isomers), chloropyridyl (isomers), methylcoumaryl (isomers) and methylquinolyl (isomers). Preferable examples of the aromatic monohydroxy compounds include phenol and cresol or the like, with the most preferable being phenol.

In the present invention, a by-produced aliphatic alcohol is withdrawn in a gaseous form, and the produced aromatic carbonates are withdrawn from a lower portion of the column in a liquid form. In the present invention, it is thus preferable for the boiling point of the by-produced aliphatic alcohol to be lower than the boiling point of each of the starting material aliphatic carbonate, the reactant aromatic monohydroxy compound, and the aromatic carbonates as a reaction product. An example of such a combination is one in which the aromatic monohydroxy compound is phenol, and $R^1$ in the aliphatic carbonate is a saturated aliphatic group having 4 to 6 carbon atoms. If the boiling point of the by-produced alcohol is low, then the temperature difference between the top and the bottom of the distillation column will become large, and hence the reaction rate may vary greatly between the stages in the distillation column; to obtain the aromatic carbonates with a yet higher yield, a yet more preferable combination is one in which the aromatic monohydroxy compound is phenol, and $R^1$ in the aliphatic carbonate is a saturated aliphatic group having 5 or 6 carbon atoms.

Since the production process according to the present invention is a process in which aromatic carbonates are produced continuously, small amounts of reaction products or the like may be fed into the continuous multi-stage distillation column together with the aliphatic carbonate and the aromatic monohydroxy compound. Examples of such reaction products include the same alcohols as the by-produced alcohol, aliphatic-aromatic carbonates, diaryl carbonates, ethers produced through decarboxylation, and Fries rearrangement products of the aromatic carbonates.

The reactant aromatic monohydroxy compound can be used in an amount such that a molar ratio thereof to an amount of the aliphatic carbonate as the starting material is in a range of from 0.01 to 1000. The reactions between the aromatic monohydroxy compound and the aliphatic carbonate are predominantly equilibrium reactions, and hence it is advantageous for the amount of the aromatic monohydroxy compound used to be high, but if this amount is increased then the reactor must be larger, and moreover a large distillation column or the like for subsequent product separation becomes necessary. The molar ratio of the reactant to the starting material is thus preferably in a range of from 0.1 to 5, more preferably from 0.5 to 5, yet more preferably from 0.5 to 2. As described in Japanese Patent Application Laid-Open No. 2000-307400, in the event of producing aromatic carbonates, when the starting material, the reactant and the catalyst are fed into a middle stage of the multi-stage distillation column, deposit may arise in the multi-stage distillation column, resulting in clogging. The reactions in the present invention are equilibrium reactions as described above, and hence a reactive distillation method using a multi-stage distillation column that enables the by-produced alcohol to be withdrawn from the reaction system so as to progressively shift the equilibrium is suitable. To carry out the process, the catalyst is thus made to be present not only at the bottom of the multi-stage distillation column, but rather in a plurality of stages, i.e. not less than two of the stages, of the continuous multi-stage distillation column.

On the other hand, if the catalyst is fed into a stage above the bottom of the multi-stage distillation column, then deposit may arise in the multi-stage distillation column, resulting in clogging as described above. As a result of assiduous studies, the present inventors have discovered that, surprisingly, in the case that an aliphatic carbonate, an aromatic monohydroxy compound and a catalyst according to the present invention are used, within the specified range of the ratio between the amounts fed in of the starting material aliphatic carbonate and the reactant aromatic monohydroxy compound, even if the starting material, the reactant and the catalyst are all fed into a stage above the bottom of the multi-stage distillation column, clogging of the multi-stage distillation column due to the catalyst, and formation of deposit on structures in the multi-stage distillation column are very unprone to occur, and reactive distillation can be carried out, and hence the aromatic carbonate yield can be increased. That is, if a specified aliphatic carbonate, a specified aromatic monohydroxy compound, and a specified catalyst are fed into a stage above the bottom of the multi-stage distillation column, and a low boiling point component containing the alcohol by-produced in the reaction is continuously withdrawn from the reaction system in a gaseous form, while the aromatic carbonate obtained from the starting material and the reactant is continuously withdrawn from the lower portion of the column in a liquid form, then clogging of the multi-stage distillation column is very unprone to occur, and moreover the reactive distillation can be carried out advantageously without azeotropy of the aliphatic carbonate and the by-produced alcohol, and hence the aromatic carbonate can be produced with a high yield. The condition for this is that the molar ratio of the reactant to the starting material fed into the multi-stage distillation column is in a range of 0.1 to 5.

The raw material fed into the reactor may contain products such as the alcohol, the aliphatic-aromatic carbonate and the diaryl carbonate, but because the present reaction is reversible, it is undesirable for the concentrations of these products to be too high, since then the raw material reaction ratio will drop.

As described above, of the reactions represented by the following reaction formulae (E1 to E4), the reaction(s) through which aromatic carbonates are produced in the present invention is/are predominantly (E1) and/or (E2), although it is also a preferable embodiment to further add a step of carrying out (E3) and (E4) to produce an industrially useful diaryl carbonate:

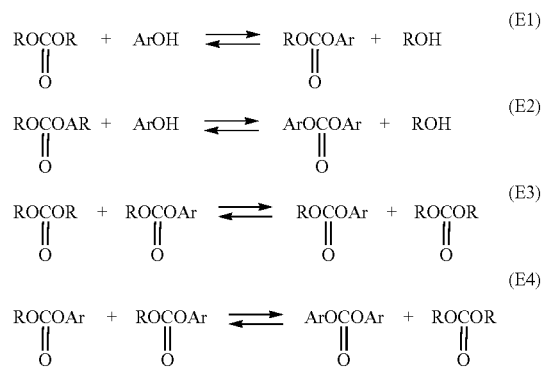

(wherein R represents an alkyl group, and Ar represents an aromatic group. Reaction formulae (E3) and (E4) are transesterification reactions between the same molecular species, with reaction formula (E4) also generally being referred to as a disproportionation reaction).

When carrying out the reactions of the above reaction formulae (E1 to E4) using the process according to the present invention, one type of each of the aliphatic carbonate and the aliphatic-aromatic carbonate may be used, or a mixture of a plurality of types may be used. Moreover, one type of the aromatic monohydroxy compound may be used, or a mixture of a plurality of types may be used. Furthermore, as shown by the above surmised reaction formulae, the production of aromatic carbonates in the present invention is carried out by feeding in predominantly the aliphatic carbonate, the aromatic monohydroxy compound and the catalyst. Solvent, impurities, and by-produced components may be present in the reaction, so long as there is no especially adverse effect on the reaction.

The alcohol by-produced through the reaction(s) represented by (E1) and/or (E2) may be recovered for recycling, and is preferably used for preparing an aliphatic carbonate. The aliphatic carbonate may be obtained using any process, although a process previously proposed by the present inventors (WO 03055840, WO 04014840) can be preferably used.

Moreover, from the viewpoint of the effective utilization of the compounds, the aliphatic carbonate produced through the reaction(s) represented by reaction formulae (E3) and/or (E4), with (E4) being particularly important, is preferably recovered for recycling, and cycled back and thus reused in the reaction(s) represented by reaction formulae (E1) and/or (E3), with (E1) being particularly important. That is, in the case of carrying out the reactions of the above reaction formulae (E1 to E4) using a first multi-stage distillation column and a second multi-stage distillation column according to the process of the present invention, it is preferable to carry out predominantly the transesterification reactions represented by formulae (E1) and (E2) in the first multi-stage distillation column, and then feed the reaction liquid containing the aromatic carbonates withdrawn from the lower portion of the column into the second multi-stage distillation column either as is or after removing the starting material and/or reactant therefrom, and carry out predominantly the disproportionation reaction represented by formula (E4), so as to produce the useful diaryl carbonate. Here, it is preferable to add a step in which the by-produced aliphatic carbonate is withdrawn from the upper portion of the distillation column in a gaseous form through distillation, and is then purified if necessary, before being reused as starting material for formula (E1).

The amount of the catalyst used in the present invention varies depending on the type of the catalyst used, the type of the reactor, the types and proportions of the aliphatic carbonate and the aromatic hydroxy compound, and reaction conditions such as the reaction temperature and the reaction pressure. The amount of the catalyst used is generally in a range of from 0.0001 to 50% by weight as a proportion of the total weight of the aliphatic carbonate and the aromatic monohydroxy compound fed in.

Many metal-containing catalysts are known as catalysts proposed for increasing the reaction rate. A publicly known transesterification catalyst can be used in the present invention. For a process of producing an aliphatic-aromatic carbonate or a mixture containing an aliphatic-aromatic carbonate and a diaryl carbonate by reacting an aliphatic carbonate and a aromatic monohydroxy compound together, examples of catalysts that have been proposed include Lewis acids such as transition metal halides and Lewis acid-forming compounds (see, for example, Japanese Patent Application Laid-Open No. 51-105032, Japanese Patent Application Laid-Open No. 56-123948, Japanese Patent Application Laid-Open No. 56-123949 (corresponding to West German Patent Application Laid-Open No. 2528412, British Patent No. 1499530, and U.S. Pat. No. 4,182,726)), tin compounds such as organo-tin alkoxides and organo-tin oxides (see, for example, Japanese Patent Application Laid-Open No. 54-48733 (corresponding to West German Patent Application Laid-Open No. 2736062), Japanese Patent Application Laid-Open No. 54-63023, Japanese Patent Application Laid-Open No. 60-169444 (corresponding to U.S. Pat. No. 4,554,110), Japanese Patent Application Laid-Open No. 60-169445 (corresponding to U.S. Pat. No. 4,552,704), Japanese Patent Application Laid-Open No. 62-277345, Japanese Patent Application Laid-Open No. 1-265063), salts and alkoxides of alkali metals and alkaline earth metals (see, for example, Japanese Patent Application Laid-Open No. 57-176932), lead compounds (see, for example, Japanese Patent Application Laid-Open No. 57-176932), complexes of metals such as copper, iron and zirconium (see, for example, Japanese Patent Application Laid-Open No. 57-183745), titanic acid esters (see, for example, Japanese Patent Application Laid-Open No. 58-185536 (corresponding to U.S. Pat. No. 4,410,464)), mixtures of a Lewis acid and a protonic acid (see, for example, Japanese Patent Application Laid-Open No. 60-173016 (corresponding to U.S. Pat. No. 4,609,501)), compounds of Sc, Mo, Mn, Bi, Te or the like (see, for example, Japanese Patent Application Laid-Open No. 1-265064), and ferric acetate (see, for example, Japanese Patent Application Laid-Open No. 61-172852).

A catalyst that catalyzes the disproportionation reaction may be used together with such a transesterification catalyst. Many such catalysts have been proposed. Examples of disproportionation reaction catalyst include Lewis acids and Lewis acid-forming transition metal compounds (see, for example, Japanese Patent Application Laid-Open No. 51-75044 (corresponding to West German Patent Application Laid-Open No. 2552907, and U.S. Pat. No. 4,045,464)), polymeric tin compounds (see, for example, Japanese Patent Application Laid-Open No. 60-169444 (corresponding to U.S. Pat. No. 4,554,110)), compounds represented by the general formula R—X(=O)OH, wherein X is selected from Sn and Ti, and R is selected from monovalent hydrocarbon groups (see, for example, Japanese Patent Application Laid-Open No. 60-169445 (corresponding to U.S. Pat. No. 4,552, 704)), mixtures of a Lewis acid and a protonic acid (see, for example, Japanese Patent Application Laid-Open No. 60-173016 (corresponding to U.S. Pat. No. 4,609,501)), lead catalysts (see, for example, Japanese Patent Application Laid-Open No. 1-93560), titanium and zirconium compounds (see, for example, Japanese Patent Application Laid-Open No. 1-265062), tin compounds (see, for example, Japanese Patent Application Laid-Open No. 1-265063), and compounds of Sc, Mo, Mn, Bi, Te or the like (see, for example, Japanese Patent Application Laid-Open No. 1-265064). Such a catalyst can also be used as a disproportionation reaction catalyst in the second multi-stage distillation column that is used additionally as described above; because catalyst is contained in the reaction liquid containing the aromatic carbonates withdrawn from the lower portion of the first multi-stage distillation column, a preferable method is to feed both the aromatic carbonates and the catalyst in the reaction liquid into the second multi-stage distillation column and carry out the disproportionation. In the present invention, the starting material and the reactant are subjected to reactive distillation using a multi-stage distillation column. If clogging of the distillation column or deposition of a catalyst-derived component on structures in the distillation column occurs, then continuous stable production may be impaired. Thus, of the above metal-containing catalysts, one that dissolves in a liquid phase in the reaction or is present in a liquid form during the reaction is preferable. Moreover, in terms of the reaction rate and the aromatic carbonate-obtaining reaction selectivity, the metal-containing catalyst is preferably an organic titanate. Examples of such organic titanates include titanium compounds represented by $Ti(OX)_4$, wherein X is a saturated aliphatic group having 4 to 6 carbon atoms or an aryl group, and titanium compound adducts represented by Ti(OX)$_4$.XOH, wherein X is a saturated aliphatic group having 4 to 6 carbon atoms or an aryl group, and also organic titanate oligomers represented by following general formulae (8) and (9). The X's in formulae (8) and (9) may each be different, and moreover may be bonded to one another. Moreover, an adduct between a compound of formula (8) or (9) and XOH, wherein X is a saturated aliphatic group having 4 to 6 carbon atoms or an aryl group, can also be preferably used:

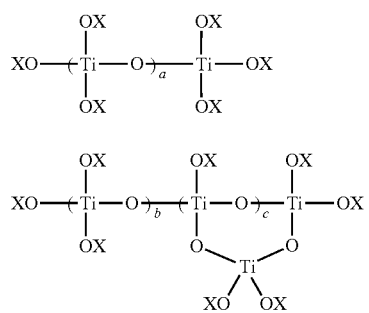

(wherein X represents a saturated aliphatic group having 4 to 6 carbon atoms or an aryl group. a represents an integer from 1 to 5. b represents an integer from 1 to 4, and c represents an integer from 0 to 4, with b+c=4).

Examples of such organic titanates include titanium tetrabutoxide (isomers), titanium tetrapentyloxide (isomers), titanium tetrahexyloxide (isomers), phenyl titanate (Ti(OPh)$_4$) (optionally in the form of a phenol adduct), and titanium tetra(methylphenoxide) (optionally in the form of a cresol adduct), and as examples of compounds represented by formula (8) or (9), compounds having the following structural formulae, for example, butoxytitanate dimer, phenoxytitanate oligomers such as phenoxytitanate dimer, phenoxytitanate trimer, and phenoxytitanate tetramer (isomers), phenoxy-salicyl-titanate oligomers such as phenoxy-salicyl-titanate dimer and phenoxy-salicyl-titanate trimer, titanate dimers from phenol and bisphenol A, and titanate trimers from phenol and bisphenol A. In terms of the solubility, compounds containing from 2 to 6 Ti atoms per molecule are preferable.

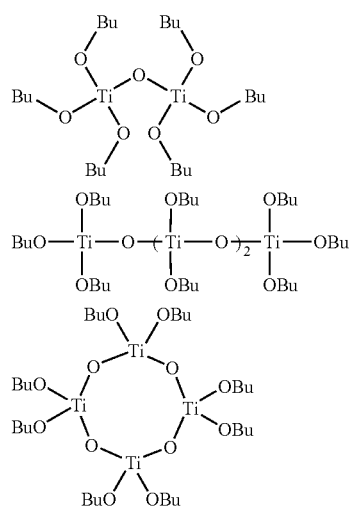

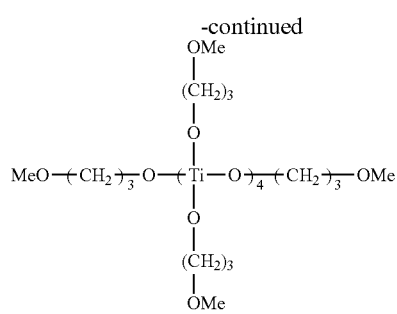

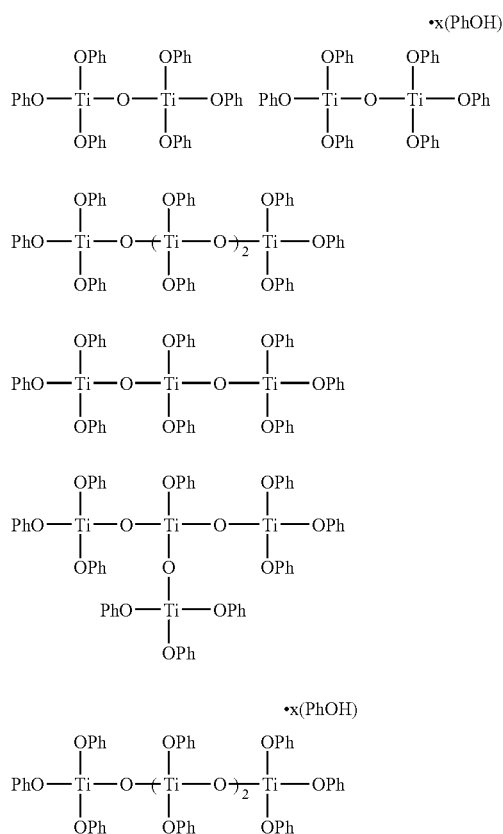

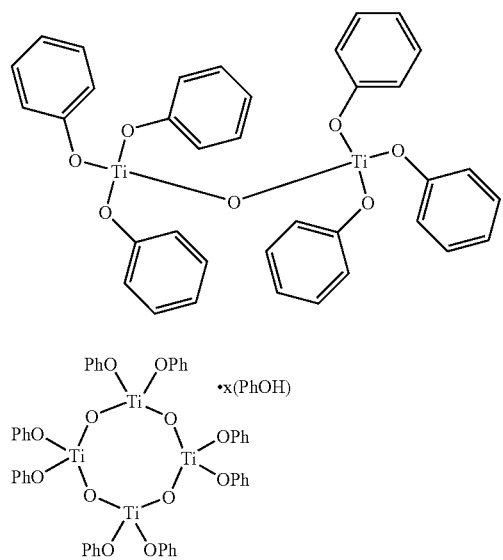

-continued

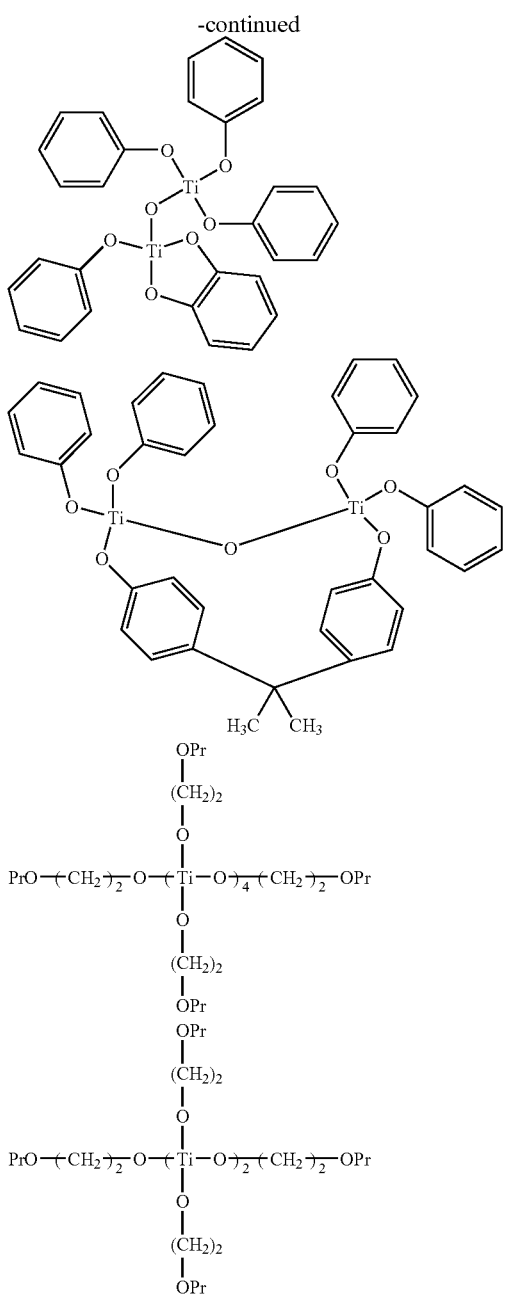

The most preferable examples include organic titanates having at least one Ti—O—Ti linkage therein. Since organic titanates have a relatively high vapor pressure, contamination with the catalyst component may occur when purifying a produced aromatic carbonate by distillation. To reduce the vapor pressure of the catalyst component, it is preferable to use an organic titanate having at least one Ti—O—Ti linkage therein. Examples of such compounds that can be used are compounds represented by above formulae (8) and (9).

A catalyst as above may of course also be used as a catalyst for the disproportionation reaction that may be additionally carried out in the second multi-stage distillation column. Moreover, the catalyst component may of course have been reacted with an organic compound present in the reaction system such as an aliphatic alcohol, the aromatic monohydroxy compound, the alkyl aryl carbonate, the diaryl carbonate or the dialkyl carbonate, or may have been subjected to heating treatment with the raw materials or products prior to the reaction, in which case low boiling point material may have been distilled off.

In the present invention, there is no need to use a reaction solvent, but a suitable inert solvent such as ether, aliphatic hydrocarbon, aromatic hydrocarbon, or halogenated aromatic hydrocarbon may be used as a reaction solvent with an objective of facilitating the reaction operation, bringing the reaction to completion or the like. Moreover, as a substance that is inert with respect to the reaction, and inert gas such as nitrogen, helium or argon may be made to be present in the reaction system, and with an objective of speeding up the distilling off of low boiling point by-products, such an inert gas, or a low melting point organic compound that is inert with respect to the reaction, may be introduced into from the lower portion of the continuous multi-stage distillation column in a gaseous form.

The aromatic carbonates produced in the present invention are aliphatic-aromatic carbonates represented by following formula (3) and/or a diaryl carbonate represented by following formula (4):

(wherein $R^2$ and $Ar^2$ in general formulae (3) and (4) are the same as $R^1$ and $Ar^1$ in the starting material and the reactant, respectively).

Examples of aliphatic-aromatic carbonates represented by the above general formula (3) include butyl phenyl carbonate (isomers), pentyl phenyl carbonate (isomers), hexyl phenyl carbonate (isomers), and butyl tolyl carbonate (isomers).

Examples of diaryl carbonates represented by the above general formula (4) include diphenyl carbonate, ditolyl carbonate (isomers), dixylyl carbonate (isomers), dinaphthyl carbonate (isomers), di(ethylphenyl)carbonate (isomers), di(propylphenyl)carbonate (isomers), di(butylphenyl)carbonate (isomers), di(trimethylphenyl)carbonate (isomers), di(methoxyphenyl)carbonate (isomers), di(chlorophenyl) carbonate (isomers), and di(nitrophenyl)carbonate (isomers).

In terms of efficiently shifting the equilibrium toward the product system, the reactor used in the present invention is preferably a multi-stage distillation column, with a continuous process using a multi-stage distillation column being particularly preferable. The multi-stage distillation column is a distillation column having a plurality of, i.e., not less than two, theoretical distillation stages therein, and may be any such one that enables continuous distillation. The multi-stage distillation column may be of any generally used type, for example a tray column using trays such as bubble-cap trays, sieve trays, valve trays or counterflow trays, or a packed column packed with any of various packings such as Raschig rings, Lessing rings, Pall rings, Berl saddles, Intalox saddles, Dixon packings, McMahon packings, Heli-Pak, Sulzer packings or Mellapak. Furthermore, a tray-packing mixed column having both a tray portion and a portion packed with packings can be preferably used. When carrying out the continuous process using the multi-stage distillation column, the starting material and the reactant are continuously fed into the continuous multi-stage distillation column, and reaction is carried out between the two in a liquid phase or a gas-liquid phase in the presence of the metal-containing catalyst in the distillation column, while a high boiling point reaction mixture containing the produced aromatic carbonate or mixture of aromatic carbonates is continuously withdrawn from the lower portion of the distillation column in a liquid form, and a low boiling point reaction mixture containing by-produced material is continuously withdrawn from the upper portion of the distillation column in a gaseous form through distillation, thus producing the aromatic carbonates.

In the present invention, because the reaction takes place in the multi-stage distillation column in which the catalyst is present, the amount of reaction products produced generally depends on the amount of hold-up in the distillation column. That is, for a given column height and column diameter, the greater the amount of liquid held up, the better, in the sense that the residence time of the reaction liquid in the distillation column, i.e. the reaction time, can be made longer. However, if the amount of liquid held up is too high, then due to the long residence time, production of by-products will be promoted, and flooding will be prone to occur. The amount of liquid held up in the distillation column used in the present invention, while possibly varying depending on the distillation conditions and the type of the distillation column, is thus generally such that the volume ratio of the amount of liquid held up to the superficial volume of the multi-stage distillation column is in a range of from 0.005 to 0.75.

In the present invention, if a reflux ratio is increased, then the effect of the aliphatic alcohol being distilled into the vapor phase is increased, and hence the concentration of the aliphatic alcohol in the withdrawn vapor can be increased. However, if the reflux ratio is increased too much, then the required thermal energy will become excessive, which is undesirable. Moreover, concentration of the aliphatic alcohol can be carried out after withdrawal from the distillation column, and hence it is not essential to carry out refluxing. The reflux ratio is thus generally in a range of from 0 to 20, preferably from 0 to 10.

In other words, when carrying out the transesterification mainly represented by reaction formula (E1), the aliphatic carbonate, the aromatic monohydroxy compound and the catalyst are fed into the multi-stage distillation column after having been mixed together or from separate positions, and the product aromatic carbonates are continuously withdrawn from the bottom of the distillation column in a liquid form, while a low boiling point component containing the by-produced alcohol is continuously withdrawn from the upper portion of the distillation column in a gaseous form through distillation. In this case, the catalyst may be fed into the multi-stage distillation column from any position, so long as this is a stage above the bottom of the distillation column. Moreover, when carrying out the optionally additionally carried out disproportionation mainly represented by formula (E4), the aliphatic-aromatic carbonate and the catalyst are fed into the multi-stage distillation column, and the product diaryl carbonate is continuously withdrawn from the bottom of the distillation column in a liquid form, while a low boiling point component containing the by-produced aliphatic carbonate is continuously withdrawn from the upper portion of the distillation column in a gaseous form through distillation.

The reaction temperature varies depending on the types of the starting material, the reactant, and the catalyst, but the temperature at the bottom of the multi-stage distillation column is generally in a range of from 50 to 350° C., preferably from 150 to 250° C. Moreover, the reaction pressure varies depending on the types of the raw material compounds used, the reaction temperature and so on, and may be any of a reduced pressure, normal pressure, or an applied pressure, but is generally in a range of from 0.1 to $2.0 \times 10^7$ Pa. For example, in the case that the aromatic monohydroxy compound is phenol, and $R^1$ in the aliphatic carbonate has 4 carbon atoms, it is preferable to carry out operation under the condition from normal pressure to an applied pressure, generally in a range of from normal pressure (approximately 101 KPa) to $2.0 \times 10^7$ Pa, and so that the low boiling point component containing the by-produced alcohol can be readily withdrawn in a gaseous form, the pressure is preferably in a range of from 110 KPa to 400 KPa, more preferably 160 to 300 KPa. On the other hand, in the case that the aromatic monohydroxy compound is phenol, and $R^1$ in the aliphatic carbonate has 5 or 6 carbon atoms so that the by-produced alcohol can be removed from the reaction system efficiently, operation is preferably carried out under the condition of reduced pressure, generally in a range of from 100 KPa to 100 Pa, and so that the temperature at the top of the distillation column does not become too low so that the low boiling point component containing the by-produced alcohol can be readily withdrawn in a gaseous form, the pressure is preferably in a range of from 100 KPa to 1 KPa, more preferably from 100 KPa to 10 KPa. The additionally carried out disproportionation reaction may be carried out similarly, with the disproportionation reaction generally preferably being carried out under a condition of reduced pressure.

A characteristic feature of the present invention is that aromatic carbonate production is carried out by continuously feeding an aliphatic carbonate as a starting material, an aromatic monohydroxy compound as a reactant, and a metal-containing catalyst into the multi-stage distillation column so as to bring about reaction, and continuously withdrawing from a lower portion of the column in a liquid form aromatic carbonates obtained from the starting material and the reactant, while continuously withdrawing out of the reaction system in a gaseous form a low boiling point component containing an alcohol by-produced in the reaction. Furthermore, there may be added a step of continuously feeding into a second multi-stage distillation column the reaction liquid withdrawn from the lower portion of the first multi-stage distillation column either as is or after removing the starting material and/or reactant therefrom, carrying out a disproportionation reaction, continuously withdrawing out of the reaction system in a gaseous form by distillation a low boiling point component containing an aliphatic carbonate by-produced in the disproportionation reaction, and continuously withdrawing from a lower portion of the second multi-stage distillation column in a liquid form aromatic carbonates including a diaryl carbonate. It is preferable to carry out this step so as to increase the yield of the diaryl carbonate, and also recycle the aliphatic carbonate by-produced in the disproportionation reaction.

The liquid containing the diaryl carbonate withdrawn from the lower portion of the second distillation column is generally introduced into a distillation column so as to purify the diaryl carbonate by distillation. The diaryl carbonate is withdrawn from an upper portion of this column in a gaseous form, and high boiling point material containing by-produced material, Fries rearrangement products of the aromatic carbonates, a catalyst component and so on is withdrawn from a lower portion of the column. This high boiling point material may be blown down as is, or only some may be blown down, with the remainder being recycled and reused as a catalyst component. In the case of reuse, removal of solid material and purification may be carried out, and moreover freshly prepared catalyst may be mixed in.

According to the production process of the present invention, a specified aliphatic carbonate is used as a starting material, and this starting material, an aromatic monohydroxy compound as a reactant, and a metal-containing catalyst are continuously fed into a stage above the bottom of a multi-stage distillation column so as to bring about reaction, and aromatic carbonates corresponding to the starting material and the reactant are continuously withdrawn from a lower portion of the column in a liquid form, while continuously withdrawing out of the reaction system in a gaseous form a low boiling point component containing an alcohol by-produced in the reaction, whereby an aromatic carbonate can be produced with an increased yield by a reactive distillation method stably and continuously under advantageous conditions and with no clogging of the multi-stage distillation column or deposition of a catalyst-derived component. This is industrially very useful.

EXAMPLES

Next, the present invention will be described in more detail by way of Examples, although the present invention is not limited to the following Examples. The acidity/alkalinity of the liquids was analyzed using litmus paper. The organic component concentrations in the liquids were measured using a gas chromatograph.
1) Gas Chromatography Analysis Method for Carbonates
Apparatus: GC-2010 system made by Shimadzu Corporation
  (1) Preparation of Analysis Sample Solution
0.4 g of the reaction solution was weighed out, and approximately 0.5 ml of dimethylformamide or acetonitrile was added. Approximately 0.05 g of diphenyl ether or toluene was further added as an internal standard, thus preparing the sample solution for gas chromatography analysis.
  (2) Gas Chromatography Analysis Conditions
Column: DB-1 (J&W Scientific)
Liquid phase: 100% dimethylpolysiloxane
Length: 30 m
Inside diameter: 0.25 mm
Film thickness: 1 μm
Column temperature: 50° C., (raised at 10° C./min), 200° C., (held for 5 min, then raised at 10° C./min), 300° C.
Injection temperature: 300° C.
Detector temperature: 300° C.
Detection method: FID
  (3) Quantitative Analysis Method
Analysis was carried out for standard samples of standard substances and calibration curves were prepared, and then quantitative analysis of the analysis sample solution was carried out based thereon.
2) Aromatic Carbonate Yield Calculation Method
Calculated as mol % produced of alkyl aryl carbonate and diary carbonate obtained based on the number of mols of the raw material (dialkyl carbonate) fed into reactor. All concentrations are shown by weight.
3) Chlorine Quantitative Analysis Method
Quantitative analysis of chlorine in the liquids was carried out using ion chromatography.
  (1) Pretreatment by Oxygen Combustion
Apparatus: TOX-100 made by Mitsubishi Chemical Corporation
Combustion temperature: 800° C.
0.1 g of the sample to be analyzed was taken, and oxygen combustion was carried out using the above apparatus.
  (2) Quantitative Analysis by Ion Chromatography Method
Apparatus: DX-300 made by Dionex
Detection method: Electrical conductivity detector
Column: AG-4A+AS-4A
Removing liquid: 12.5 mmol/L $H_2SO_4$
Eluate: 10 mmol/L $Na_2B_4O_7$ The residue obtained from the pretreatment was prepared into an aqueous solution, and then quantitative measurement of the chlorine in the analysis sample was carried out based on a calibration curve that has been prepared using a standard chlorine sample.

EXAMPLES

The present invention will now be described by way of Examples. Unless otherwise stated, pressures indicate absolute pressures, not gauge pressures.

Example 1

Figure 2:
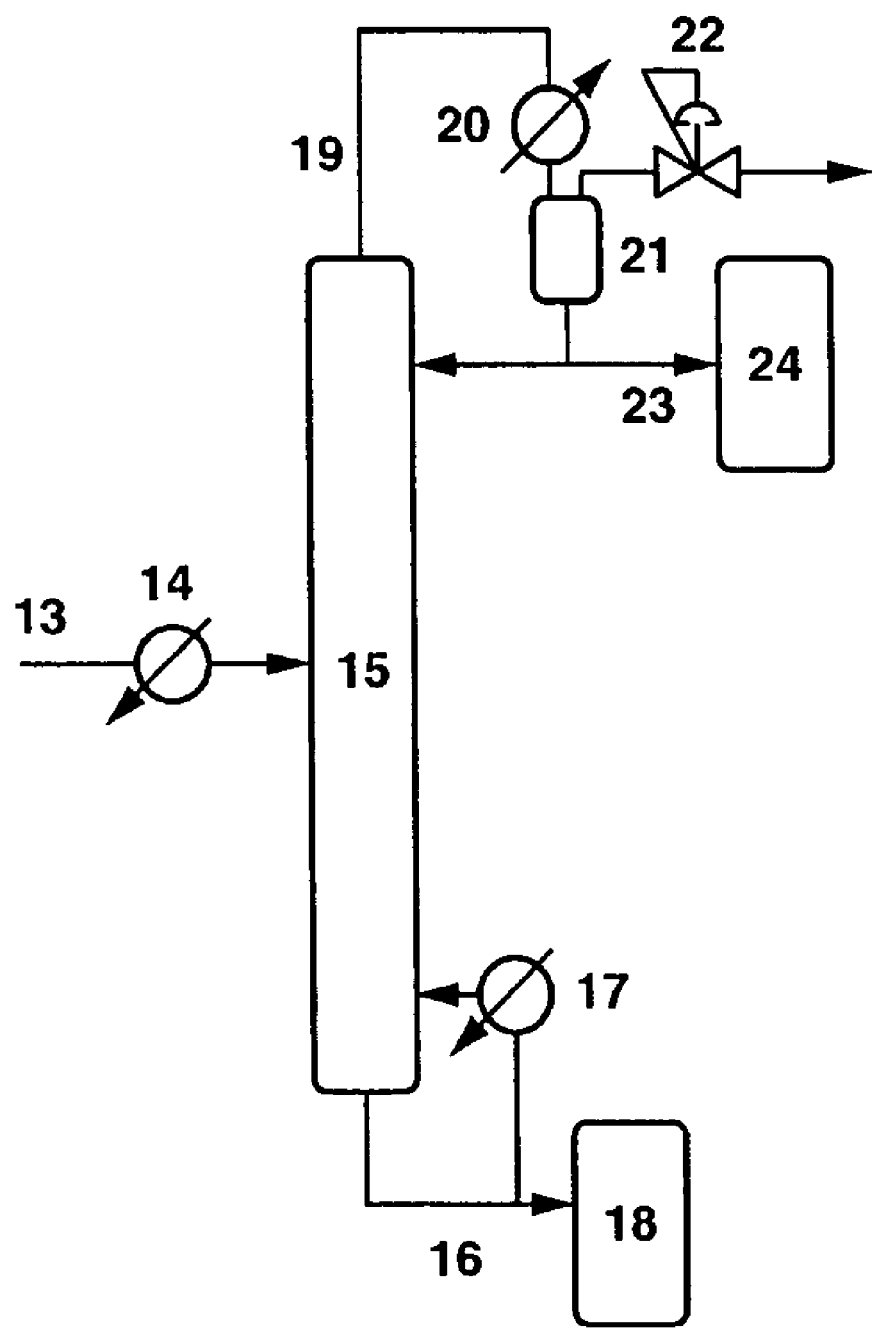
FIG. 2 is a process flow diagram for diaryl carbonate production according to the present invention.

[Production of Aromatic Carbonates by Transesterification Reaction]
Production of aromatic carbonates by transesterification reaction was carried out using an apparatus as shown in FIG. 1. A mixed liquid containing di(2-ethylbutyl)carbonate, phenol, and titanium tetraphenoxide as a catalyst (adjusted such that di(2-ethylbutyl)carbonate/phenol weight ratio in mixed liquid was 70/30 (molar ratio 0.96), and Ti concentration was approximately 600 ppm) was fed continuously in a liquid form at approximately 112 g/Hr from a transfer line 1 via a preheater 2 into a middle stage of a continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through a conduit 4 and a reboiler 5. The temperature of the liquid at the bottom of the continuous multi-stage distillation column 3 was made to be approximately 200° C., the pressure at the top of the column approximately 27 KPa, and the reflux ratio approximately 5. Gas distilled off from the top of the continuous multi-stage distillation column 3 was passed through a conduit 7, condensed by a condenser 8, and continuously withdrawn at approximately 16 g/Hr from a conduit 11. The liquid from the bottom of the column was continuously withdrawn through the conduit 4 into a storage tank 6 at approximately 95 g/Hr. A composition of the liquid withdrawn from the conduit 11 was 2-ethyl-1-butanol and phenol as main components thereof. A composition of the liquid withdrawn into the storage tank 6 contained approximately 49.5% by weight of di(2-ethylbutyl)carbonate, approximately 27% by weight of 2-ethylbutyl phenyl carbonate, and approximately 2% by weight of diphenyl carbonate. After operation, the inside of the distillation column was examined, but no clogging, deposit or the like was found. The di(2-ethylbutyl)carbonate conversion ratio was approximately 39.7%, and the phenol conversion ratio was approximately 41%.
[Production of Diaryl Carbonate by Disproportionation Reaction]
Production of diaryl carbonate by disproportionation reaction was carried out using an apparatus as shown in FIG. 2. Liquid withdrawn from the storage tank 6 in the above process was fed continuously in a liquid form at approximately 100 g/Hr from a transfer line 13 via a preheater 14 into a middle stage of a continuous multi-stage distillation column 15 which has an inside diameter being 2 inches and a length being 2 m, and which was packed with 10 stages of sieve trays, and reaction was carried out (as a catalyst, the catalyst contained in the liquid was used as is). The heat required for the reaction and distillation was fed in by circulating liquid in the lower portion of the column through a conduit 16 and a reboiler 17. The temperature of the liquid at the bottom of the continuous multi-stage distillation column 15 was made to be approximately 230° C., the pressure at the top of the column approximately 27 KPa, and the reflux ratio approximately 2. Gas distilled off from the top of the continuous multi-stage distillation column 15 was passed through a conduit 19, condensed by a condenser 20, and continuously withdrawn from a conduit 23. The liquid from the bottom of the column was continuously withdrawn through the conduit 16 into a storage tank 18. A composition of the liquid withdrawn from the conduit 23 contained 2-ethyl-1-butanol, phenol and di(2-ethylbutyl)carbonate. The liquid withdrawn into the storage tank 18 contained approximately 45% by weight of 2-ethylbutyl phenyl carbonate, and approximately 55% by weight of diphenyl carbonate.

[Purification of Diaryl Carbonate]

Figure 3:
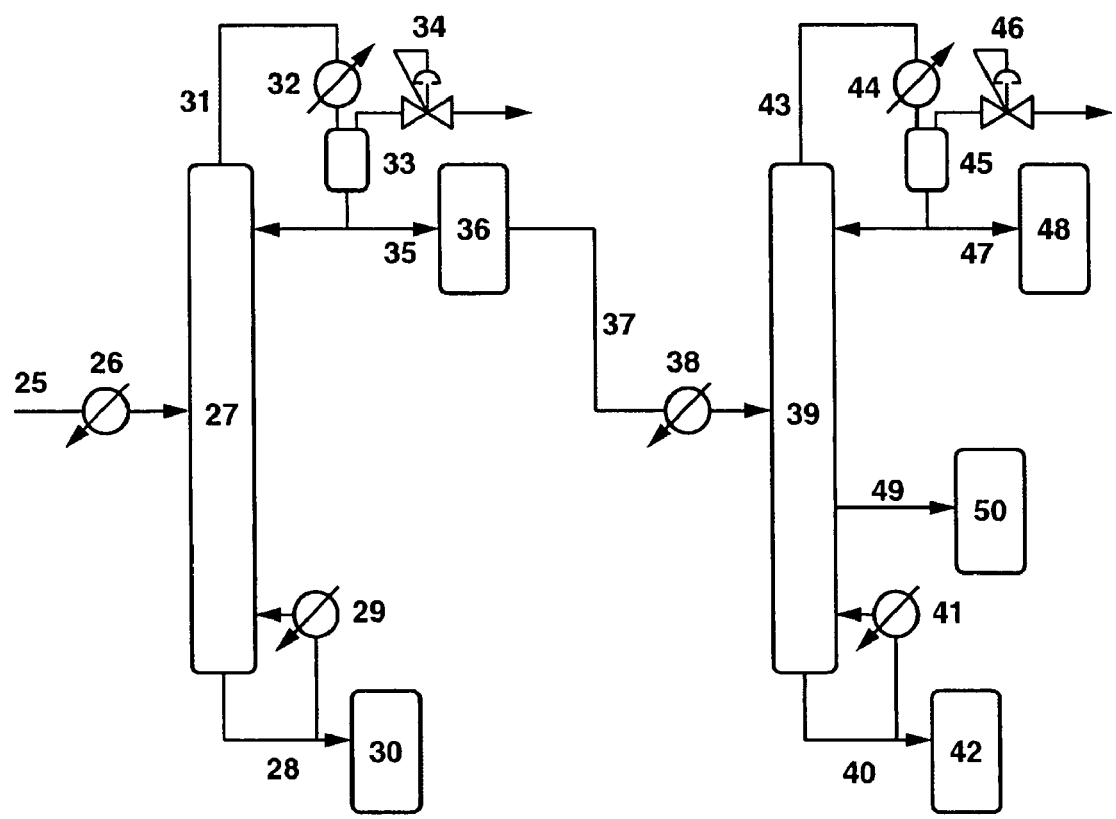
FIG. 3 is a process flow diagram for diaryl carbonate purification according to the present invention.

Purification of the diaryl carbonate was carried out using an apparatus as shown in FIG. 3. Liquid from the storage tank 18 was fed continuously at approximately 100 g/Hr from a conduit 25 via a preheater 26 into a middle stage of a continuous multi-stage distillation column 27 which has an inside diameter being 2 inches and a length being 2 m, and which was packed with Dixon packings (6 mm diameter), and separation by distillation was carried out. The heat required for the separation by distillation was fed in by circulating liquid in the lower portion of the column through a conduit 28 and a reboiler 29. The temperature of the liquid at the bottom of the continuous multi-stage distillation column 27 was made to be approximately 210° C., the pressure at the top of the column approximately 1.5 KPa, and the reflux ratio approximately 1. Gas distilled off from the top of the continuous multi-stage distillation column 27 was passed through a conduit 31, condensed by a condenser 32, and continuously withdrawn from a conduit 35 into a storage tank 36. The liquid from the bottom of the column was continuously withdrawn through the conduit 28 into a storage tank 30. A composition of the liquid withdrawn from the conduit 35 contained di(2-ethylbutyl)carbonate, 2-ethylbutyl phenyl carbonate and diphenyl carbonate. Liquid from the storage tank 36 was then fed continuously at approximately 200 g/Hr from a conduit 37 via a preheater 38 into a middle stage of a continuous multi-stage distillation column 39 which has an inside diameter being 2 inches and a length being 4 m, and which was packed with Dixon packings (6 mm diameter), and separation by distillation was carried out. The heat required for the separation by distillation was fed in by circulating liquid in the lower portion of the column through a conduit 40 and a reboiler 41. The temperature of the liquid at the bottom of the continuous multi-stage distillation column 39 was made to be approximately 210° C., the pressure at the top of the column approximately 3 KPa, and the reflux ratio approximately 2. Gas distilled off from the top of the continuous multi-stage distillation column 39 was passed through a conduit 43, condensed by a condenser 44, and continuously withdrawn from a conduit 47 into a storage tank 48. Some of the liquid from an intermediate portion of the column was continuously withdrawn through a conduit 49 into a storage tank 50. The liquid from the bottom of the column was continuously withdrawn through the conduit 40 into a storage tank 42 at approximately 1 g/Hr. A composition of the liquid withdrawn from the conduit 47 contained approximately 83% by weight of 2-ethylbutyl phenyl carbonate, and approximately 17% by weight of diphenyl carbonate. A composition of the liquid withdrawn from the conduit 49 was approximately 100% by weight of diphenyl carbonate. The diphenyl carbonate withdrawn from the conduit 49 was a white solid at room temperature, and chlorine was not detected therein.

Example 2

(Preparation of Catalyst)

3400 g (10 mol) of tetra-n-butoxytitanium and 1700 g of n-butanol were put into a reaction flask equipped with a stirrer, a thermometer, a heating/cooling apparatus and a reflux condenser, and the liquid was cooled to 0° C. while being mixing well. While keeping the temperature of the liquid at 0° C., a mixed liquid of 90 g (5 mol) of water and 2000 g of n-butanol was gradually added over 1 hour. After the addition had been completed, the temperature was raised to 80° C., and heating and stirring were carried out for 5 hours. The temperature of the liquid was reduced to room temperature (approximately 20° C.), and then the flask was connected to a rotary evaporator equipped with a vacuum controller and a vacuum pump, and an oil bath for heating. While keeping the temperature of the liquid at 80° C., a low boiling point component was distilled off under a reduced pressure of approximately 25 KPa. Once distillate had almost completely stopped being produced, the temperature was gradually increased to 230° C., and the pressure was further reduced to 1 Pa, and then once it had been verified that distillate had almost completely stopped being produced, the pressure was returned to normal pressure with nitrogen, and the temperature of the liquid was returned to room temperature (approximately 20° C.), whereupon approximately 2750 g of a pale yellow viscous liquid was obtained (the results of elemental analysis were C, 52.3%, H, 9.9%, O: 20.4%, and Ti: 17.4%, and hence deducting oxygen originating from BuO groups, the number of bridging oxygens was 1 per 2 Ti atoms, i.e. there was one Ti—O—Ti linkage). It is surmised that the liquid was a mixture having butyl titanate dimer [(BuO)$_3$—Ti—O—Ti—(OBu)$_3$] as a main component thereof.

The flask was once again equipped with a stirrer, a thermometer, a heating/cooling apparatus and a reflux condenser, and the liquid was heated with stirring such that the temperature of the liquid became 80° C. While keeping the temperature of the liquid at 80° C., 4700 g (50 mol) of phenol that had been dehydrated through distillation in advance was gradually added. After the addition had been completed, the liquid was heated to 180° C., thus distilling of a low boiling point component. Once distillate had almost completely stopped being produced, the temperature of the liquid was gradually increased to 230° C., and the evaporating component was distilled off. A vacuum controller and a vacuum pump were connected to the flask, the pressure was gradually reduced to 1 Pa, and the evaporating component was distilled off. Thereafter, the flask was taken out from the oil bath, and cooled to room temperature (approximately 20° C.), and the pressure in the flask was returned to normal pressure with nitrogen. Approximately 4300 g of a tango solid was obtained. The results of elemental analysis were C, 64.5%, H, 4.5%, O: 16.7%, and Ti: 14.3%, and hence it is surmised that the solid was a mixture having a phenol adduct of phenyl titanate dimer [(PhO)$_3$—Ti—O—Ti—(OPh)$_3$.2PhOH] as a main component thereof. This tango solid was taken as catalyst A.

[Production of Aromatic Carbonates by Transesterification Reaction]

Production of aromatic carbonates by transesterification reaction was carried out using the apparatus as shown in FIG. 1. A mixed liquid containing di(2-ethylbutyl)carbonate, phenol, and above catalyst A (adjusted such that di(2-ethylbutyl)carbonate/phenol weight ratio in mixed liquid was 70/30 (molar ratio 0.96), and Ti concentration was approximately 2000 ppm) was fed continuously in a liquid form at approximately 120 g/Hr from the transfer line 1 via the preheater 2 into a middle stage of the continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 180° C., the pressure at the top of the column approximately 13 KPa, and the reflux ratio approximately 4. Gas distilled off from the top of the continuous multi-stage distillation column 3 was passed through the conduit 7, condensed by the condenser 8, and continuously withdrawn at approximately 30 g/Hr from a conduit 11. The liquid from the bottom of the column was continuously withdrawn through the conduit 4 into the storage tank 6 at approximately 90 g/Hr. A composition of the liquid withdrawn from the conduit 11 was 2-ethyl-1-butanol and phenol as main components thereof. A composition of the liquid withdrawn into the storage tank 6 contained approximately 57% by weight of di(2-ethylbutyl)carbonate, approximately 31% by weight of 2-ethylbutyl phenyl carbonate, and approximately 3% by weight of diphenyl carbonate. After operation, the inside of the distillation column was examined, but no clogging, deposit or the like was found. The di(2-ethylbutyl)carbonate conversion ratio was approximately 39%, and the phenol conversion ratio was approximately 41%.

[Production of Diaryl Carbonates by Disproportionation Reaction]

Production of diary carbonate by disproportionation reaction was carried out using the apparatus as shown in FIG. 2. Liquid withdrawn from the storage tank 6 in the above process was fed continuously in a liquid form at approximately 100 g/Hr from a transfer line 13 via a preheater 14 into a middle stage of a continuous multi-stage distillation column 15 which has an inside diameter being 2 inches and a length being 2 m, and which was packed with 10 stages of sieve trays, and reaction was carried out (as a catalyst, the catalyst contained in the liquid was used as is). The heat required for the reaction and distillation was fed in by circulating liquid in the lower portion of the column through the conduit 16 and the reboiler 17. The temperature of the liquid at the bottom of the continuous multi-stage distillation column 15 was made to be approximately 230° C., the pressure at the top of the column approximately 27 KPa, and the reflux ratio approximately 2. Gas distilled off from the top of the continuous multi-stage distillation column 15 was passed through the conduit 19, condensed by the condenser 20, and continuously withdrawn from the conduit 23. The liquid from the bottom of the column was continuously withdrawn through the conduit 16 into the storage tank 18. A composition of the liquid withdrawn from the conduit 23 contained 2-ethyl-1-butanol, phenol and di(2-ethylbutyl)carbonate. A composition of the liquid withdrawn into the storage tank 18 contained approximately 45% by weight of 2-ethylbutyl phenyl carbonate, and approximately 55% by weight of diphenyl carbonate.

[Purification of Diaryl Carbonate]

Purification of the diaryl carbonate was carried out using the apparatus as shown in FIG. 3. Liquid from the storage tank 18 was fed continuously at approximately 100 g/Hr from the conduit 25 via the preheater 26 into a middle stage of the continuous multi-stage distillation column 27 which has an inside diameter being 2 inches and a length being 2 m, and which was packed with Dixon packings (6 mm diameter), and separation by distillation was carried out. The heat required for the separation by distillation was fed in by circulating liquid in the lower portion of the column through the conduit 28 and the reboiler 29. The temperature of the liquid at the bottom of the continuous multi-stage distillation column 27 was made to be approximately 210° C., the pressure at the top of the column approximately 1.5 KPa, and the reflux ratio approximately 1. Gas distilled off from the top of the continuous multi-stage distillation column 27 was passed through the conduit 31, condensed by the condenser 32, and continuously withdrawn from the conduit 35 into the storage tank 36. The liquid from the bottom of the column was continuously withdrawn through the conduit 28 into the storage tank 30. A composition of the liquid withdrawn from the conduit 35 contained di(2-ethylbutyl)carbonate, 2-ethylbutyl phenyl carbonate and diphenyl carbonate. Liquid from the storage tank 36 was then fed continuously at approximately 200 g/Hr from the conduit 37 via the preheater 38 into a middle stage of the continuous multi-stage distillation column 39 which has an inside diameter being 2 inches and a length being 4 m, and which was packed with Dixon packings (6 mm diameter), and separation by distillation was carried out. The heat required for the separation by distillation was fed in by circulating liquid in the lower portion of the column through the conduit 40 and the reboiler 41. The temperature of the liquid at the bottom of the continuous multi-stage distillation column 39 was made to be approximately 210° C., the pressure at the top of the column approximately 3 KPa, and the reflux ratio approximately 2. Gas distilled off from the top of the continuous multi-stage distillation column 39 was passed through the conduit 43, condensed by the condenser 44, and continuously withdrawn from the conduit 47 into the storage tank 48. Some of the liquid from an intermediate portion of the column was continuously withdrawn through the conduit 49 into the storage tank 50. The liquid from the bottom of the column was continuously withdrawn through the conduit 40 into the storage tank 42 at approximately 1 g/Hr. A composition of the liquid withdrawn from the conduit 47 contained approximately 83% by weight of 2-ethylbutyl phenyl carbonate, and approximately 17% by weight of diphenyl carbonate. The liquid withdrawn from the conduit 49 was approximately 100% by weight of diphenyl carbonate. The diphenyl carbonate withdrawn from the conduit 49 was a white solid at room temperature, and chlorine was not detected therein.

Example 3

[Production of Aromatic Carbonates by Transesterification Reaction]

Production of aromatic carbonates by transesterification reaction was carried out using the apparatus as shown in FIG. 1. A mixed liquid containing di(2-ethylbutyl)carbonate, phenol, and titanium tetraphenoxide as a catalyst (adjusted such that di(2-ethylbutyl)carbonate/phenol weight ratio in mixed liquid was 65/35 (molar ratio 0.75), and Ti concentration was approximately 600 ppm) was fed continuously in a liquid form at approximately 53 g/Hr from the transfer line 1 via the preheater 2 into a middle stage of the continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 200° C., the pressure at the top of the column approximately 27 KPa, and the reflux ratio approximately 5.

Gas distilled off from the top of the continuous multi-stage distillation column 3 was passed through conduit 7, condensed by the condenser 8, and continuously withdrawn at approximately 9 g/Hr from the conduit 11. The liquid from the bottom of the column was continuously withdrawn through the conduit 4 into the storage tank 6 at approximately 44 g/Hr. A composition of the liquid withdrawn from the conduit 11 had 2-ethyl-1-butanol and phenol as main components thereof. A composition of the liquid withdrawn into the storage tank 6 contained approximately 42% by weight of di(2-ethylbutyl)carbonate, approximately 27% by weight of 2-ethylbutyl phenyl carbonate, and approximately 2% by weight of diphenyl carbonate. After operation, the inside of the distillation column was examined, but no clogging, deposit or the like was found. The di(2-ethylbutyl)carbonate conversion ratio was approximately 41%, and the phenol conversion ratio was approximately 44%.

Example 4

[Production of Aromatic Carbonates by Transesterification Reaction]

Production of aromatic carbonates by transesterification reaction was carried out using the apparatus as shown in FIG. 1. A mixed liquid containing di(2-ethylbutyl)carbonate, phenol, the liquid collected in the storage tank 42 in Example 1 as a catalyst (which was a reddish brown Ti-containing solid), and 200 ppm of 2-ethylbutyl phenyl carbonate (adjusted such that di(2-ethylbutyl)carbonate/phenol weight ratio in mixed liquid was 71/29 (molar ratio 1), and Ti concentration was approximately 1000 ppm) was fed continuously in a liquid form at approximately 100 g/Hr from the transfer line 1 via the preheater 2 into a middle stage of the continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 210° C., the pressure at the top of the column approximately 50 KPa, and the reflux ratio approximately 5. Gas distilled off from the top of the continuous multi-stage distillation column 3 was passed through the conduit 7, condensed by the condenser 8, and continuously withdrawn at approximately 14 g/Hr from the conduit 11. The liquid from the bottom of the column was continuously withdrawn through the conduit 4 into the storage tank 6 at approximately 86 g/Hr. A composition of the liquid withdrawn from the conduit 11 had 2-ethyl-1-butanol and phenol as main components thereof. A composition of the liquid withdrawn into the storage tank 6 contained approximately 47% by weight of di(2-ethylbutyl)carbonate, approximately 32% by weight of 2-ethylbutyl phenyl carbonate, and approximately 1% by weight of diphenyl carbonate. After operation, the inside of the distillation column was examined, but no clogging, deposit or the like was found. The di(2-ethylbutyl)carbonate conversion ratio was approximately 42%, and the phenol conversion ratio was approximately 42%.

Example 5

[Production of Aromatic Carbonates by Transesterification Reaction]

Production of aromatic carbonates by transesterification reaction was carried out using the apparatus as shown in FIG. 1. A mixed liquid containing di(2-ethylbutyl)carbonate, phenol, and titanium tetraphenoxide as a catalyst (adjusted such that di(2-ethylbutyl)carbonate/phenol weight ratio in mixed liquid was 55/45 (molar ratio 0.5), and Ti concentration was approximately 600 ppm) was fed continuously in a liquid form at approximately 78 g/Hr from the transfer line 1 via the preheater 2 into a middle stage of a continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 200° C., the pressure at the top of the column approximately 27 KPa, and the reflux ratio approximately 5. Gas distilled off from the top of the continuous multi-stage distillation column 3 was passed through the conduit 7, condensed by the condenser 8, and continuously withdrawn at approximately 9 g/Hr from the conduit 11. The liquid from the bottom of the column was continuously withdrawn through the conduit 4 into the storage tank 6 at approximately 69 g/Hr. A composition of the liquid withdrawn from the conduit 11 contained 2-ethyl-1-butanol and phenol. A composition of the liquid withdrawn into the storage tank 6 contained approximately 37% by weight of di(2-ethylbutyl)carbonate, approximately 22% by weight of 2-ethylbutyl phenyl carbonate, and approximately 1% by weight of diphenyl carbonate. After operation, the inside of the distillation column was examined, but no clogging, deposit or the like was found. The di(2-ethylbutyl)carbonate conversion ratio was approximately 38%, and the phenol conversion ratio was approximately 40%.

Example 6

[Production of Aromatic Carbonates by Transesterification Reaction]

Production of aromatic carbonates by transesterification reaction was carried out using the apparatus as shown in FIG. 1. A mixed liquid containing di(2-ethylbutyl)carbonate, phenol, and titanium tetraphenoxide as a catalyst (adjusted such that di(2-ethylbutyl)carbonate/phenol weight ratio in mixed liquid was 83/17 (molar ratio 2), and Ti concentration was approximately 600 ppm) was fed continuously in a liquid form at approximately 86 g/Hr from the transfer line 1 via the preheater 2 into a middle stage of the continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 200° C., the pressure at the top of the column approximately 27 KPa, and the reflux ratio approximately 5. Gas distilled off from the top of the continuous multi-stage distillation column 3 was passed through the conduit 7, condensed by the condenser 8, and continuously withdrawn at approximately 10 g/Hr from the conduit 11. The liquid from the bottom of the column was continuously withdrawn through the conduit 4 into the storage tank 6 at approximately 76 g/Hr. A composition of the liquid withdrawn from the conduit 11 had 2-ethyl-1-butanol and phenol as main components thereof. A composition of the liquid withdrawn into the storage tank 6 contained approximately 62% by weight of di(2-ethylbutyl)carbonate, approximately 29% by weight of 2-ethylbutyl phenyl carbonate, and approximately 1% by weight of diphenyl carbonate. After operation, the inside of the distillation column was examined, but no clogging, deposit or the like was found. The di(2-ethylbutyl)carbonate conversion ratio was approximately 34%, and the phenol conversion ratio was approximately 34%.

Example 7

[Production of Aromatic Carbonates by Transesterification Reaction]

Production of aromatic carbonates by transesterification reaction was carried out using the apparatus as shown in FIG. 1. A mixed liquid containing di(n-pentyl)carbonate, phenol, and titanium tetraphenoxide as a catalyst (adjusted such that di(n-pentyl)carbonate/phenol weight ratio in mixed liquid was 68/32 (molar ratio 1), and Ti concentration was approximately 600 ppm) was fed continuously in a liquid form at approximately 92 g/Hr from the transfer line 1 via the preheater 2 into a middle stage of the continuous multi-stage distillation column 3 which has an inside diameter being 2 inches and a length being 2 m, and which was packed with 10 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 230° C., the pressure at the top of the column approximately 60 KPa, and the reflux ratio approximately 5. Gas distilled off from the top of the continuous multi-stage distillation column 3 was passed through the conduit 7, condensed by the condenser 8, and continuously withdrawn at approximately 12 g/Hr from the conduit 11. The liquid from the bottom of the column was continuously withdrawn through the conduit 4 into the storage tank 6 at approximately 80 g/Hr. A composition of the liquid withdrawn from the conduit 11 had n-pentanol and phenol as main components thereof. A composition of the liquid withdrawn into the storage tank 6 contained approximately 45% by weight of di(n-pentyl)carbonate, approximately 33% by weight of n-pentyl phenyl carbonate, and approximately 1% by weight of diphenyl carbonate. After operation, the inside of the distillation column was examined, but no clogging, deposit or the like was found. The di(n-pentyl)carbonate conversion ratio was approximately 42%, and the phenol conversion ratio was approximately 42%.

Example 8

[Production of Aromatic Carbonates by Transesterification Reaction]

Production of aromatic carbonates by transesterification reaction was carried out using the apparatus as shown in FIG. 1. A mixed liquid containing di(n-butyl)carbonate, phenol, and titanium tetraphenoxide as a catalyst (adjusted such that di(n-butyl)carbonate/phenol weight ratio in mixed liquid was 65/35 (molar ratio 1), and Ti concentration was approximately 600 ppm) was fed continuously in a liquid form at approximately 110 g/Hr from the transfer line 1 via the preheater 2 into a middle stage of the continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 200° C., the pressure at the top of the column approximately 110 KPa, and the reflux ratio approximately 4. Gas distilled off from the top of the continuous multi-stage distillation column 3 was passed through the conduit 7, condensed by the condenser 8, and continuously withdrawn at approximately 17 g/Hr from the conduit 11. The liquid from the bottom of the column was continuously withdrawn through the conduit 4 into the storage tank 6 at approximately 93 g/Hr. A composition of the liquid withdrawn from the conduit 11 had n-butanol, di(n-butyl)carbonate and phenol as main components thereof. A composition of the liquid withdrawn into the storage tank 6 contained approximately 52% by weight of di(n-butyl)carbonate, approximately 22% by weight of butyl phenyl carbonate, and approximately 0.5% by weight of diphenyl carbonate. After operation, the inside of the distillation column was examined, but no clogging, deposit or the like was found. The di(n-butyl)carbonate conversion ratio was approximately 29%, and the phenol conversion ratio was approximately 31%.

Example 9

(Preparation of Catalyst)

3400 g (10 mol) of tetra-n-butoxytitanium and 1700 g of n-butanol were put into a reaction flask equipped with a stirrer, a thermometer, a heating/cooling apparatus and a reflux condenser, and the liquid was cooled to 0° C. while being mixing well. While keeping the temperature of the liquid at 0° C., a mixed liquid of 90 g (5 mol) of water and 2000 g of n-butanol was gradually added over 1 hour. After the addition had been completed, the temperature was raised to 80° C., and heating and stirring were carried out for 5 hours. The temperature of the liquid was reduced to room temperature (approximately 20° C.), and then the flask was connected to a rotary evaporator equipped with a vacuum controller and a vacuum pump, and an oil bath for heating. While keeping the temperature of the liquid at 80° C., a low boiling point component was distilled off under a reduced pressure of approximately 25 KPa. Once distillate had almost completely stopped being produced, the temperature was gradually increased to 230° C., and the pressure was further reduced to 1 Pa, and then once it had been verified that distillate had almost completely stopped being produced, the pressure was returned to normal pressure with nitrogen, and the temperature of the liquid was returned to room temperature (approximately 20° C.), whereupon approximately 2750 g of a pale yellow viscous liquid was obtained (the results of elemental analysis were C, 52.3%, H, 9.9%, O: 20.4%, and Ti: 17.4%, and hence deducting oxygen originating from BuO groups, the number of bridging oxygens was 1 per 2 Ti atoms, i.e. there was one Ti—O—Ti linkage). It is surmised that the liquid was a mixture having butyl titanate dimer [(BuO)$_3$—Ti—O—Ti—(OBu)$_3$] as a main component thereof. This liquid was taken as catalyst B.

[Production of Aromatic Carbonates by Transesterification Reaction]

Production of aromatic carbonates by transesterification reaction was carried out using the apparatus as shown in FIG. 1. A mixed liquid containing di(n-butyl)carbonate, phenol, and above catalyst B (adjusted such that di(n-butyl)carbonate/phenol weight ratio in mixed liquid was 65/35 (molar ratio 1), and Ti concentration was approximately 600 ppm) was fed continuously in a liquid form at approximately 83 g/Hr from the transfer line 1 via the preheater 2 into a middle stage of the continuous multi-stage distillation column 3 which has an inside diameter being 2 inches and a length being 2 m, which was packed with 10 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 220° C., the pressure at the top of the column approximately 120 KPa, and the reflux ratio approximately 4. Gas distilled off from the top of the continuous multi-stage distillation column 3 was passed through the conduit 7, condensed by the condenser 8, and continuously withdrawn at approximately 5 g/Hr from the conduit 11. The liquid from the bottom of the column was continuously withdrawn through the conduit 4 into the storage tank 6 at approximately 77 g/Hr. A composition of the liquid withdrawn from the conduit 11 had n-butanol and phenol as main components thereof. A composition of the liquid withdrawn into the storage tank 6 contained approximately 54% by weight of di(n-butyl)carbonate, approximately 15% by weight of butyl phenyl carbonate, and approximately 1% by weight of diphenyl carbonate. After operation, the inside of the distillation column was examined, but no clogging, deposit or the like was found. The di(n-butyl)carbonate conversion ratio was approximately 21%, and the phenol conversion ratio was approximately 22%.

Example 10

[Production of Aromatic Carbonates by Transesterification Reaction]

Production of aromatic carbonates by transesterification reaction was carried out using the apparatus as shown in FIG. 1. A mixed liquid containing di(2-ethylbutyl)carbonate, phenol, and titanium tetraphenoxide as a catalyst (adjusted such that di(2-ethylbutyl)carbonate/phenol weight ratio in mixed liquid was 54.5/45.5 (molar ratio 0.49), and Ti concentration was approximately 600 ppm) was fed continuously in a liquid form at approximately 77 g/Hr from the transfer line 1 via the preheater 2 into a middle stage of the continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 200° C., the pressure at the top of the column approximately 27 KPa, and the reflux ratio approximately 5. Gas distilled off from the top of the continuous multi-stage distillation column 3 was passed through the conduit 7, condensed by the condenser 8, and continuously withdrawn at approximately 9 g/Hr from the conduit 11. The liquid from the bottom of the column was continuously withdrawn through the conduit 4 into the storage tank 6 at approximately 69 g/Hr. A composition of the liquid withdrawn from the conduit 11 had 2-ethyl-1-butanol and phenol as main components thereof. A composition of the liquid withdrawn into the storage tank 6 contained approximately 38% by weight of di(2-ethylbutyl)carbonate, approximately 21% by weight of 2-ethylbutyl phenyl carbonate, and approximately 1% by weight of diphenyl carbonate. After operation, the inside of the distillation column was examined, whereupon it was found that there was a thin solid deposit on the sieve trays. The di(2-ethylbutyl)carbonate conversion ratio was approximately 37%, and the phenol conversion ratio was approximately 41%.

Example 11

[Production of Aromatic Carbonates by Transesterification Reaction]

The process of Example 1 was carried out up to and including the disproportionation, and then liquid withdrawn from the conduit 21 and collected in the storage tank 24 was subjected to separation by distillation, and di(2-ethylbutyl)carbonate was recovered.

Production of aromatic carbonates by transesterification reaction was carried out using the apparatus as shown in FIG. 1. A mixed liquid containing di(2-ethylbutyl)carbonate recovered as described above, phenol, and titanium tetraphenoxide as a catalyst (adjusted such that di(2-ethylbutyl)carbonate/phenol weight ratio in mixed liquid was 70/30 (molar ratio 0.96), and Ti concentration was approximately 600 ppm) was fed continuously in a liquid form at approximately 112 g/Hr from the transfer line 1 via the preheater 2 into a middle stage of the continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 200° C., the pressure at the top of the column approximately 27 KPa, and the reflux ratio approximately 5. Gas distilled off from the top of the continuous multi-stage distillation column 3 was passed through the conduit 7, condensed by the condenser 8, and continuously withdrawn at approximately 16 g/Hr from the conduit 11. The liquid from the bottom of the column was continuously withdrawn through the conduit 4 into the storage tank 6 at approximately 95 g/Hr. A composition of the liquid withdrawn from the conduit 11 had 2-ethyl-1-butanol and phenol as main components thereof. A composition of the liquid withdrawn into the storage tank 6 contained approximately 49.5% by weight of di(2-ethylbutyl)carbonate, approximately 27% by weight of 2-ethylbutyl phenyl carbonate, and approximately 2% by weight of diphenyl carbonate. After operation, the inside of the distillation column was examined, but no clogging, deposit or the like was found. The di(2-ethylbutyl)carbonate conversion ratio was approximately 39.7%, and the phenol conversion ratio was approximately 41%.

Example 12

[Production of Aromatic Carbonates by Transesterification Reaction]

Production of aromatic carbonates by transesterification reaction was carried out using the apparatus as shown in FIG. 1. A mixed liquid containing di(n-butyl)carbonate, phenol, and titanium tetraphenoxide as a catalyst (adjusted such that di(n-butyl)carbonate/phenol weight ratio in mixed liquid was 38/62 (molar ratio 0.33), and Ti concentration was approximately 10000 ppm) was fed continuously in a liquid form at approximately 110 g/Hr from the transfer line 1 via the preheater 2 into a middle stage of the continuous multi-stage distillation column 3 which has an inside diameter being 2 inches and a length being 2 m, and which was packed with 10 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 220° C., the pressure at the top of the column approximately 300 KPa, and the reflux ratio approximately 5. Gas distilled off from the top of the continuous multi-stage distillation column 3 was passed through the conduit 7, condensed by the condenser 8, and continuously withdrawn at approximately 1 g/Hr from the conduit 11. The liquid from the bottom of the column was continuously withdrawn through the conduit 4 into the storage tank 6 at approximately 109 g/Hr. A composition of the liquid withdrawn from the conduit 11 had n-butanol and phenol as main components thereof. A composition of the liquid withdrawn into the storage tank 6 contained approximately 30% by weight of di(n-butyl)carbonate, approximately 5% by weight of butyl phenyl carbonate, and approximately 0.1% by weight of diphenyl carbonate. After operation, the inside of the distillation column was examined, whereupon it was found that there was a thin solid deposit on the sieve trays. The di(n-butyl)carbonate conversion ratio was approximately 14%, and the phenol conversion ratio was approximately 14%.

Comparative Example 1

[Production of Aromatic Carbonates by Transesterification Reaction]

Production of aromatic carbonates by transesterification reaction was carried out using the apparatus as shown in FIG. 1. A mixed liquid containing di(n-butyl)carbonate and phenol (di(2-ethylbutyl)carbonate/phenol weight ratio in mixed liquid 70/30 (molar ratio 0.96)) was fed continuously in a liquid form at approximately 112 g/Hr from a transfer line 1 via the preheater 2 into a middle stage of the continuous multi-stage distillation column 3 which has an inside diameter being 2 inches and a length being 4 m, and which was packed with 20 stages of sieve trays in a lower portion of the column and Dixon packings (6 mm diameter) in an upper portion of the column, titanium tetraphenoxide as a catalyst was fed into the bottom of the column such that the Ti concentration based on the total amount of materials fed in was approximately 600 ppm, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 200° C., the pressure at the top of the column approximately 27 KPa, and the reflux ratio approximately 5. Gas distilled off from the top of the continuous multi-stage distillation column 3 was passed through the conduit 7, condensed by the condenser 8, and continuously withdrawn at approximately 1 g/Hr from the conduit 11. The liquid from the bottom of the column was continuously withdrawn through the conduit 4 into the storage tank 6 at approximately 110 g/Hr. A composition of the liquid withdrawn from the conduit 11 had 2-ethyl-1-butanol and phenol as main components thereof. A composition of the liquid withdrawn into the storage tank 6 contained approximately 60% by weight of di(2-ethylbutyl)carbonate, approximately 4% by weight of 2-ethylbutyl phenyl carbonate, and approximately 0.1% by weight of diphenyl carbonate. The di(2-ethylbutyl)carbonate conversion ratio was approximately 7%, and the phenol conversion ratio was approximately 6%.

Comparative Example 2

[Production of Aromatic Carbonates by Transesterification Reaction]

Production of aromatic carbonates by transesterification reaction was carried out using the apparatus as shown in FIG. 1. A mixed liquid containing dimethyl carbonate, phenol, and titanium tetraphenoxide as a catalyst (adjusted such that dimethyl carbonate/phenol weight ratio in mixed liquid was 73/27 (molar ratio 2.8), and Ti concentration was approximately 1000 ppm) was fed continuously in a liquid form at approximately 126 g/Hr from the transfer line 1 via the preheater 2 into a middle stage of the continuous multi-stage distillation column 3 which has an inside diameter being 2 inches and a length being 2 m, and which was packed with 10 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 203° C., the pressure at the top of the column approximately 0.9 MPa, and the reflux ratio approximately 0.8. Gas distilled off from the top of the continuous multi-stage distillation column 3 was passed through the conduit 7, condensed by the condenser 8, and continuously withdrawn at approximately 42 g/Hr from the conduit 11. The liquid from the bottom of the column was continuously withdrawn through the conduit 4 into the storage tank 6 at approximately 84 g/Hr. A composition of the liquid withdrawn from the conduit 11 had dimethyl carbonate, methanol and phenol as main components thereof. A composition of the liquid withdrawn into the storage tank 6 contained approximately 3.4% by weight of methyl phenyl carbonate, and approximately 0.1% by weight of diphenyl carbonate. After operation, the inside of the distillation column was examined, whereupon it was found that there was a thin solid deposit on the sieve trays. The dimethyl carbonate conversion ratio was approximately 2.3%, and the phenol conversion ratio was approximately 6.6%.

Comparative Example 3

[Production of Aromatic Carbonates by Transesterification Reaction]

Production of aromatic carbonates by transesterification reaction was carried out using the apparatus as shown in FIG. 1. A mixed liquid containing diheptyl carbonate, phenol, and titanium tetraphenoxide as a catalyst (adjusted such that diheptyl carbonate/phenol weight ratio in mixed liquid was 73/27 (molar ratio 1), and Ti concentration was approximately 600 ppm) was fed continuously in a liquid form at approximately 101 g/Hr from the transfer line 1 via the preheater 2 into a middle stage of the continuous multi-stage distillation column 3 which has an inside diameter being 2 inches and a length being 2 m, and which was packed with 10 stages of sieve trays in a lower portion of the column and Dixon packings (6 mm diameter) in an upper portion of the column, and reaction was carried out. The heat required for the reaction and distillation was fed in by circulating liquid in the lower portion of the column through the conduit 4 and the reboiler 5. The temperature of the liquid at the bottom of the continuous multi-stage distillation column 3 was made to be approximately 210° C., the pressure at the top of the column approximately 27 KPa, and the reflux ratio approximately 4. Gas distilled off from the top of the continuous multi-stage distillation column 3 was passed through the conduit 7, condensed by the condenser 8, and continuously withdrawn at approximately 5 g/Hr from the conduit 11. The liquid from the bottom of the column was continuously withdrawn through the conduit 4 into the storage tank 6 at approximately 96 g/Hr. A composition of the liquid withdrawn from the conduit 11 had heptanol and phenol as main components thereof. A composition of the liquid withdrawn into the storage tank 6 contained approximately 7.1% by weight of heptyl phenyl carbonate, and approximately 0.1% by weight of diphenyl carbonate. The diheptyl carbonate conversion ratio was approximately 10%, and the phenol conversion ratio was approximately 10%.

INDUSTRIAL APPLICABILITY

According to the present invention, a specified aliphatic carbonate and a specified aromatic monohydroxy compound are reacted together using a reactive distillation method in the presence of a catalyst, whereby an aromatic carbonate can be produced continuously with a high yield.

I claim:

1. A process for the production of an aromatic carbonate, comprising:
continuously feeding an aliphatic carbonate represented by following general formula (1) as a starting material, an aromatic monohydroxy compound represented by following general formula (2) as a reactant, and a metal-containing catalyst into a stage above a bottom of a first multi-stage distillation column so as to bring about reaction; and
continuously withdrawing from a reaction system in a gaseous form a low boiling point component containing an alcohol by-produced in the reaction, and continuously withdrawing from a lower portion of the column in a liquid form an aromatic carbonate represented by following general formula (3) obtained from the starting material and the reactant,

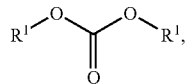
(1)

Ar¹OH (2), wherein R¹ in general formulae (1) and (2) represents an aliphatic group having 4 to 6 carbon atoms, and Ar¹ represents an aromatic group having 5 to 30 carbon atoms,

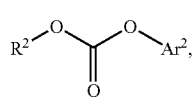
(3)

wherein R² and Ar² in general formula (3) are the same as R¹ and Ar¹ in the starting material and the reactant, respectively, wherein said metal-containing catalyst is dissolved in a liquid phase in said reaction, or is present in a liquid form during said reaction, and said metal-containing catalyst comprises an organic titanate having at least one Ti—O—Ti linkage therein.

2. The process according to claim 1, wherein said aromatic carbonate comprises a diaryl carbonate represented by following general formula (4):

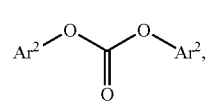
(4)

wherein Ar² in general formula (4) is the same as Ar¹ in the reactant.

3. The process according to claim 1, wherein R¹ in the aliphatic carbonate represented by general formula (1) is a saturated aliphatic group having 4 to 6 carbon atoms.

4. The process according to claim 1, wherein R¹ in the aliphatic carbonate represented by general formula (1) is a saturated aliphatic group having 5 or 6 carbon atoms.

5. The process according to claim 1, wherein R¹ in the aliphatic carbonate represented by general formula (1) is an alkyl group.

6. The process according to claim 1, wherein the aromatic monohydroxy compound represented by general formula (2) comprises phenol.

7. The process according to claim 1, wherein the column bottom temperature in said distillation column is in a range of from 150 to 250° C.

8. The process according to claim 1, wherein a molar ratio of the reactant to the starting material fed into said multi-stage distillation column is in a range of from 0.1 to 5.

9. The process according to claim 1, wherein the first multi-stage distillation column has not less than two theoretical distillation stages therein, and the catalyst is made to be present in at least two of the stages.

10. The process according to claim 2, further comprising the steps of:
continuously feeding into a second multi-stage distillation column the reaction liquid withdrawn from the lower portion of the first multi-stage distillation column in the process according to claim 1 either as is or after removing the starting material and/or reactant therefrom, so as to carry out a disproportionation reaction;
continuously withdrawing in a gaseous form by distillation a low boiling point component containing an aliphatic carbonate by-produced in the reaction; and
continuously withdrawing from a lower portion of the second multi-stage distillation column in a liquid form the diaryl carbonate represented by the general formula (4).

11. The process according to claim 10, wherein the steps according to claim 13 are performed to recycle the aliphatic carbonate for use as the starting material.

12. The process according to claim 11, wherein R¹ in the aliphatic carbonate represented by general formula (1) is a saturated aliphatic group having 5 or 6 carbon atoms.

13. The process according to claim 12, wherein R¹ in the aliphatic carbonate represented by general formula (1) is an alkyl group.

14. The process according to claim 13, wherein the aromatic monohydroxy compound represented by general formula (2) comprises phenol.

15. The process according to claim 14, wherein the column bottom temperature in said distillation column is in a range of from 150 to 250° C.

16. The process according to claim 15, wherein a molar ratio of the reactant to the starting material fed into said multi-stage distillation column is in a range of from 0.1 to 5.

17. The process according to claim 16, wherein the first multi-stage distillation column has not less than two theoretical distillation stages therein, and the catalyst is made to be present in at least two of the stages.

* * * * *